United States Patent [19]
Galili et al.

[11] Patent Number: 5,879,675
[45] Date of Patent: Mar. 9, 1999

[54] COMPOSITIONS AND METHODS FOR VACCINES COMPRISING α-GALACTOSYL EPITOPES

[75] Inventors: Uri Galili, Wayne, Pa.; Patricia M. Repik, West Trenton, N.J.

[73] Assignee: Medical College of Pennsylvania and Hahnemann University, Philadelphia, Pa.

[21] Appl. No.: 704,548

[22] PCT Filed: Mar. 13, 1995

[86] PCT No.: PCT/US95/03156

§ 371 Date: Sep. 11, 1996

§ 102(e) Date: Sep. 11, 1996

[87] PCT Pub. No.: WO95/24924

PCT Pub. Date: Sep. 21, 1995

Related U.S. Application Data

[63] Continuation-in-part of Ser. No. 213,200, Mar. 15, 1994, abandoned.

[51] Int. Cl.$^6$ .......... A61K 39/395; A61K 39/12; A61K 45/00; A01N 63/00

[52] U.S. Cl. .......... 424/93.1; 424/184.1; 424/218.1; 424/816; 424/159.1; 424/277.1; 424/155.1; 424/156.1; 424/278.1

[58] Field of Search ................ 424/93.1, 277.1, 424/278.1, 155.1, 156.1, 184.1, 218.1, 816

[56] References Cited

U.S. PATENT DOCUMENTS 4,008,317  2/1977  Gits ............................................ 424/89

OTHER PUBLICATIONS

Gollogly et al, Neoplasma 43(5):285–89, 1996.
Tremont–Lukats et al, Gynecologic Oncology 64:207–212, 1997.
Galili et al, Vaccine, 14:321–28, 1996.
Gorelik et al, Cancer Res. 57:332–336, 1997.
Qu et al, Glycobiology, 7(6):803–809, 1997.
LaTemple et al, Cancer Res. 56:3069–3074, 1996.
Boduszek et al. J. Med. Chem. 37:3969–76, 1994.
Azadi et al, Glycobiology 5(8):783–789, 1995.
Bystryn, Cancer & Metastasis Rev. 9:81–91, 1990.
Siemann, Rodent Tumor Models in Exptal, Cancer Therapy. Ed. Kallman pp. 12–15, 1987.
Avila, et al. 1989, *Journal of Immunology*, vol. 142, No. 8, "Immunogenic Galα 1—3gal carbohydrate epitopes are present on pathogenic american Trypanosoma and Leishmania", pp. 1818–2834 (15 Apr. 1989).
Galili et al., *Proceedings National Academy Sciences USA*, vol. 84, "Evolutionary relationship between the natural anti–Gal antibody and the Galα 1→3 Gal epitope in primates", pp. 1369–1273 (Mar. 1987).
Galili et al., *J Exp. Med.*, vol. 162, "Human Natural Anti–Galactosyl IgG II. The specific Recognition of α(1→3)–Linked Galactose Residues", pp. 573–582 (Aug. 1985).

U. Galili, *Immunology Today*, vol. 14, No. 10, "Interaction of the natural anti–Gal antibody with α–galactosyl epitopes: a major obstacle for xenotransplantation in humans", pp. 480–482 (1993).
M.S. Sandrin et al., *Proceedings National Academy Sciences USA*, vol. 90, "Anti–pig IgM antibodies in human serum react predominantly with Gal (α1–3) Gal epitopes", pp. 11391–11395 (Dec. 1993).
U. Galili et al., *Journal of Biological Chemistry*, vol. 263, "Man, apes, and Old World Monkey differ from other mammals in the expression of α–Galactosyl epitopes on nucleated cells" pp. 17755–17762 (25 Nov. 1988).
R.J. Winand et al., *Journal of Immunology*, vol. 151, No. 7, "Xenogeneic thyroid–stimulating hormone–like activty of the human natural nati–gal antibody", pp. 3923–3934 (01 Oct. 1993).
U. Galili, *Immunopathology*, vol. 15, "Evolution and pathophysiology of the human natural anti–α–galactosyl IgG (anti–gal) antibody" pp. 155–171 (1993).
P.M. Repik, *Journal of General Virology*, "Differential host–dependent expression of α–galactosyl epitopes on viral glycoproteins: a study of eastern equine encephalitis virus as a model", pp. 1177–1181 (9114).
Basu et al., "Enzymatic Synthesis of Blood Group B–related Pentaglycosylceramide by an α–Galactosyltransferase from Rabbitt Bone Marrow", *J. Biol. Chem.* (1973) 248:1700–1706.
Blanken et al., "Biosynthesis of Terminal Galα1–3Galβ1–4GalcNAc–R Oligosaccharide Sequences on Glycoconjugates", *J. Biol. Chem.* (1985) 260:12927–12934.
Brand et al., "Sequential Passage of Influenza Virus in Embryonated Eggs or Tissue Culture: Emergence of Mutants", *Virology* (1980) 107:424–433.
Burke et al., "Purification and Composition of the Proteins from Sindbis Virus Grown in Chick and BHK Cells", *J. Virol.* (1976) 20:676–686.
Chang and Trent, "Nucleotide Sequence of the Genome Region Encoding the 26S mRNA of Eastern Equine Encephalomyelitis Virus and the Deduced Amino Acid Sequence of the Viral Structural Proteins", *J. Gen. Virol.* (1987) 68:2129–2142.
Chien et al., "Isolation and Characterization of a Heptaglycosylceramide from Bovine Erythrocyte Membranes", *J. Lipid Res.* (1979) 20:669–673.
Davin et al., Anti–α–Galactosyl Antibodies and Immune Complexes in Children With Henoch–Schönlein Purpura or IgA *Nephropathy Kidney Int.* (1987) 31:1132–1139.

(List continued on next page.)

*Primary Examiner*—Nita Minnifield
*Attorney, Agent, or Firm*—Seidel, Gonda Lavorgna & Monaco, PC

[57] ABSTRACT

The invention encompasses methods and compositions for inducing an immune response in an anti-Gal synthesizing animal including viral and tumor antigens manipulated to express α-galactosyl epitopes.

25 Claims, 18 Drawing Sheets

OTHER PUBLICATIONS

Doerfler, "Expression of the *Autographa California* Nuclear Polyhedrosis Virus Genome in Insect Cells: Homologous Viral and Heterologous Vertebrate Genes–The Baculovirus Vector System" *Curr. Topics Microbiol. Immunol.* (1986) 131:51–68.

Egge et al., "Immunochemistry of I/i–active Oligo– and Polyglycosylceramides from Rabbit Erythrocyte Membranes, 1985, J. Biol. Chem.", J. Biol. Chem. (1985) 260:4927–4935.

Elices et al., "Purification and Characterization of a UDP–Gal:β–DGal(1,4)–D–GlcNAcα(1–3)–Galactosyltransferase from Ehrlich Ascites Tumor Cells", J. Biol. Chem. (1986) 261:6064–6072.

Eto et al., "Chemistry of Lipid of the Posthemolytic Residue or Stroma of Erythrocytes", *J. Biochem.* (Tokyo) (1968) 64:205–213.

Folch et al., "A Simple Method For The Isolation and Purification of Total Lipides From Animal Tissues", *J. Biol. Chem.* (1957) 226:497–509.

Galili et al., "A Unique Natural Human IgG Antibody With Anti–α–Galactosyl Specificity", *J. Exp. Med.* (1984) 160:1519–1531.

Galili et al., "Human Natural Anti–α–Galactosyl IgG II", *J. Exp. Med.* (1985) 162:573–582.

Galili et al., "Identification of Erythrocyte Galα1–3Gal Glycosphingolipids With a Mouse Monoclonal Antibody, Gal–13", *J. Biol. Chem.* (1987) 262(10):4683–4688.

Galili et al., "The Human Natural Anti–Gal IgG III", *J. Exp. Med.* (1987) 165:693–704.

Galili and Swanson, "Gene Sequences Suggest Inactivation of α–1, 3–Galactosyltransferase in Catharrhines After the Divergence of Apes from Monkeys", *Proc. Natl. Acad. Sci. USA* (1991) 88:7401–7404.

Galili et al., "One Percent of Human Circulating B lymphocytes are Capable of Producing the Natural Anti–Gal Antibody", Blood (1993) 82(5):2485–2493.

Geyer et al., "Major Oligosaccharides in the Glycoprotein of Friend Murine Leukemia Virus: Structure Elucidation by One– and Two–Dimensional Proton Nuclear Magnetic Resonance and Methylation Analysis", *Biochemistry* (1984) 23:5628–5637.

Honma et al., "Isolation and Partial Structural Characterization of Macroglycolipid from Rabbit Erythrocyte Membranes", *J. Biochem.* (Tokyo) (1981) 90:1187–1196.

Joziasse et al., "Bovine α1–3–Gal;actosyltransferase: Isolation and Characterization on cDNA Clone", *J. Biol. Chem.* (1989) 264:14290–14297.

Joziasse et al., "Murine α1.3–Galactosyltransferase", *J. Biol. Chem.* (1992) 267:5534–5541.

Joziasse, "Mammalian Glycosyltransferases: Genomic Organization and Protein Structure", *Glycobiology* (1992) 2:271–277.

Keil et al., Carbohydrates of Influenza Virus, Structural Elucidation of the Individual Glycans of the FPV Hemagglutinin by Two–Dimensional $^1$H n.m.r. and Methylation Analysis:, EMBO J. (1985) 4(10):2711–2720.

Kinney et al., "Recombinate Vaccinia/Venezuelan Equine Encephalitis (VEE) Virus Expresses VEE Structural Proteins", *J. Gen. Virol.* (1988) 69:3005:3013.

Klenk, "Influence of Glycosylation on Antigenicity of Viral Proteins", Regenmortal and Neurath (Eds.) *The Basis For Serodiagnosis and Vaccines,* Elsevier Publishers B.V., N.Y, (1990) pp. 25–37.

Klenk and Rott, "Cotranslational and Posttranslational Processing of Viral Glycoproteins" Basle et al. (Eds) *Curr. Topics Microbiol. Immunol.* Springer–Verlang, Berlin Heidelberg, New York (1980) 90:19–48.

Koblet, "The Merry–Go–Round" :Alphaviruses Between Vertebrate and Invertebrate Cells, *Adv. Virus Res.* (1990) 38:343–402.

Kornfeld et al., "Assembly of Asparagine–Linked Oligosaccharides", *Ann. Rev. Biochem* (1985) 54:631:664.

Kuroda et al., "Expression of the Influenza Virus Haemagglutinin in Insect Cells by a Baculovirus Vector", *EMBO J.* (1986) 5:1359:1365.

Lanzavecchia, "Identifying Strategies for Immune Intervention", *Science* (1993) 230:937–944.

Livingston "Active Specific Immunotherapy in the Treatment of Patients With Cancer" *Immunology and Allergy Clinics of North America* (1991) 11(2):401:423.

Mackett et al., "The Construction and Characterization of Vaccinia Virus Recombinants Expressing Foreign Genes", Glover (Ed.) *DNA Cloning, A Practival Approach,* IRL Press, Washington, D.C. (1985) vol. II, 191–211.

Masibay et al., "Mutational Analysis of the Golgi Retention Signal of Bovine β–1–4–Galactosyltransferase" *J. Biol. Chem.* (1993) 268:9908:9916.

Melnick, "Virus Vaccines: An Overview", Dressman et al., (Eds.) *High Technology Route to Virus Vaccines* (1985) 1–14.

Mitchell et al., "Active Specific Immunotherapy of Melanoma With Allogeneic Cell Lysates" Bystran et al., (eds.), *Specific Immunotherapy of Cancer With Vaccines,* New York Academy of Sciences, NY, (1993) 690:153–166.

Morton et al., "Polyvalent Melanoma Vaccine Improves Survival of Patients with Metastatic Melanoma", Bystran et al., (eds.) *Specific Immunotherapy of Cancer With Vaccines,* New York Academy of Sciences, NY, (1993) 690: 120–134.

Orgra et al., "Secretory Antibody Response to Viral Vaccines", *Prog. Med. Virol.* (1990) 37:156:189.

Panicali et al., "Construction of Live Vaccines by Using Genetically Engineered Poxviruses: Biological Activity Recombinant Vaccinia Virus Expressing Influenza Virus Hemagglutinin" *Proc. Natl. Acad. Sci. USA* (1983) 80:5364:5368.

Pardoll, "Cancer Vaccines", *Immunol. Today* (1993) 14(6):310:316.

Parvin et al., "Measurement of the Mutation Rates of Animal Viruses: Influenza A Virus and Poliovirus Type 1", *J. Virol.* (1986) 59:377–383.

Paulson et al., "Structure, Localization, and Control of Cell Type–Specific Glycosylation", *J. Biol. Chem.* (1989) 264:17615:17618.

Possee, "Cell–Surface Expression of Influenza Virus Haemagglutinin in Insect Cells using a Caculovirus Vector", *Virus Research* (1986) 5:43–59.

Rademacher et al., "Glycobiology", *Ann. Rev. Biochem.* (1988) 57:785–838.

Ribgy, "Review Article, Clonong Vectors Derived from Animal Viruses", *J. Gen. Virol.* (1983) 64:255–266.

Robbins et al., "Proposal for a Common Oligosaccharide Intermediate in the Synthesis of Membrane Glycoproteins", *Cell* (1977) 12:893–900.

Rothstein, "Cloning in Yeast", Glover (Ed.) *DNA Cloning, A Practical Approach,* IRL Press, Washington, D.C. (1985) vol. II, 45–66.

Sandrin et al., "Anti–Pig IgM Antibodies in Human Serum React Predominantly With Gal ($\alpha$1–3) Gal Epitopes", *Proc. Natl. Acad.Sci. USA* (1993) 90:11391:11395.

Sanger et al., "DNA Sequencing With Chain–Terminating Inhibitors", *Proc. Natl. Acad. Sci USA* (1977) 74(12):5463:5467.

Santer et al., "N–Linked Oligosaccharide Changes With Oncogenic Transformation Require Sialylation of Multiantennae", *Eur. J. Biochem.* (1989) 181:249–260.

Schlesinger and Schlesinger, "Formation and Assembly f Alpohavirus Glycoproteins", *The Togaviridae and Flaviviridae,* Plenum Press, N.Y. (ed.) (1986) 121–148.

Schmaljohn et al., "Characterization of Hantaan Virion, the Prototype Virus of Hemorrhagic Fever with Renal Syndrome", *J. Infect. Dis.* (1983) 148(6):1005–1012.

Seed et al., "Molecular Cloning of the CD2 Antigen, the T–Cell Erythrocyte Receptor, By a Rapid Immunoselection Procedure", *Proc. Natl. Acad. Sci. USA* (1987) 84:3365–3369.

Small et al., "Intranasal Vaccination With Recombinant Vaccinia Containing Influenza Hemagglutinin Prevents Both Influenza Virus Pneumonia and Nasal Infection Intradermal Vaccination Prevents Only Viral Pneumonia", Quinnan (Ed.) *Vaccinia Viruses as Vectors for Vaccine Antigens,* Elsevier, NY (1985) 175–177.

Stellnar et al., "Determination of Aminosugar Linages in Glycolipids by Methylation", *Arch. Biochem. Biophys.* (1973) 155:464–472.

Stevenson, "Tumor Vaccines", *FASEB J.* (1991) 5:(2250–2257).

Thall et al., "Distribution of Gal$\alpha$1$\rightarrow$3GAL$\beta$$\rightarrow$4G1cNAc Residues on Secreted Mammalian Glycoproteins (thyroglobulin, Fibrinogen, and Immunoglobulin G) As Measured by a Sensitive Solid–Phase Radioimmunoassay", *Biochemistry* (1990) 29:3959–3065.

Ward et al., "Completion of the Amino Acid Sequence of a Hong Kong Influenza Hemagglutinin Heavy Chain: Sequence of Cyanogen Bromide Fragment CN1", *Virology* (1980) 103:37–53.

Winland et al., "Xenogeneic Thyroid–Stimulating Hormone–Like Activity of the Human Natural Anti–Gal Antibody" *J. of Immunology* (1993) 151(7):3923–3934.

Winter et al., "Nucleotide Sequence of the Haemagglutinin Gene of a Human Influenza Virus H1 Subtype", *Nature* 292:72–75.

Wood et al., "Immunochemical Studies of the Combining Sites of the Two Isolectins, $A_4$ and $B_4$, Isolated From *Bandeiraea Simplicifolia", Arch. Biochem. Biophys.* (1979) 198:1–11.

Larsen et al., "Isolation of a cDNA Encoding a Murine UDPgalactose:$\beta$–D–Galactosyl–1–1–4–N–Acetyl–D– Glucosaminide $\alpha$–1,3–Galactosyltransferase: Expression Cloning by Gene Transfer", *Proc. Natl. Acad. Sci USA* (1989(86:8227–8231.

```
                                                                        GAGAAAATA
    M  N  V  K  G  K  V  I  L  S  M  L  V  V  S  T  V  I  V  V           20
 1  ATGAATGTCAAAGGAAAAGTAATTCTGTCTGATGCTGGTTGTCTCAACTGTGATTGTTGTG
    .........G.............................A................C...

F  W  E  Y  I  N  S  P  E  G  S  F  L  W  I  Y  H  S  K  N           40
21  TTTTGGGAATATATCAACAGCCCAGAGAGGCTCTTTCTTGTGGATATATCACTCAAAGAAC
    .........G................C.........................A..A.TT

P  E  V  D  D  S  S  A  Q  K  D  W  F  P  G  W  F  N  N             60
41  CCAGAAGTTGATGACAGCAGTGCTCAGAAGGACTGGTTTCCTGGCTGGTTTAACAAT
    ........G...G..A...ATGG..................C..AA........A...

G  I  H  N  Y  Q  Q  E  E  E  D  T  D  K  E  K  G  R  E  E          80
61  GGGATCCACAATTATCAACAAGAGGAAGAAGACACAGACAAAGAAAAGGAAGAGAGGAG
    ........C.........G..........CA..C..T....AGG..CGG..G....G..T...A..T..GA

E  Q  K  E  D  D  T  E  L  R  L  D  W  F  N  P  K                  100
81  GAACAAAAAGAAGATGACACAGAGCTTCGGGCTATGGGGACTTGGTTTAATCCAAAG
    ..AT.GC..TTG.-------............C..A........................C..........

K  R  P  E  V  M  T  V  T  Q  W  K  A  P  V  V  W  E  G  T         120
101 AAACGCCCAGAGGTTATGACAGTGACCCAATGGAAGGCGCCGGTTGTGTGGGAAGGCACT
    .....C......G..T..T......................CG........A...........

Y  N  K  A  I  L  E  N  Y  Y  A  K  Q  K  I  T  V  G  L  T         140
121 TACAACAAAGCCATCCTAGAAAATTATTATGCCAAACAGAAAATTACCGTGGGGTTGACG
    ..TG....C......TC..G.......................G..C..C........C..T......A

V  F  A  I  G  R  Y  I  E  H  Y  L  E  E  F  V  T  S  A  N         160
141 GTTTTTGCTATTGGAAGATATATTGAGCATTACTTGGAGGAGTTCGTAACATCTGCTAAT
    ..G.....G..G.......AG..C...................A..A..C..TC..GGAG.....G..C

R  Y  F  M  V  G  H  K  V  I  F  Y  V  M  V  D  D  V  S  K         180
161 AGGTACTTCATGGTCGGCCACAAAGTCATATTTTATGTCATGGTGGATGATGTCTCCAAG
    .T............T......TCGG..........C.........A..A..C..CAC....CG.
```

FIG. 9B

```
                                                                                          200
181  A   P   F   I   E   L   G   P   L   R   S   F   K   V   F   E   V   K   P   E
     GCGCCGTTTATAGAGCTGGGTCCTCTGCGTTCCTTCAAAGTGTTTGAGGTCAAGCCAGAG
     AT...TG.CG.GC.C....AAC......A.A........AC.........A....G.T.T...

220
201  K   R   W   Q   D   I   S   M   M   R   M   K   T   I   G   E   H   I   L   A
     AAGAGGTGGCAAGACATCAGGATGATGCGTATGAAGACCATCGGGGAGCACATCTTGGCC
     ...........G..T.................................C.........C...

240
221  H   I   Q   H   E   V   D   F   L   F   C   M   D   V   D   Q   V   F   Q   D
     CACATCCAACACGAGGTTGACTTCCTCTTCTGCATGGATGTGGACCAGGTCTTCCAAGAC
     ..............G...............CT...A..A........C.....T......

260
241  H   F   G   V   E   T   L   G   Q   S   S   A   Q   L   Q   A   W   W   Y   K
     CATTTTGGGGTAGAGACCCTGGGCCAGTCGGCTGCTCAGCTACAGGCCTGGTGGTACAAG
     A..C..C.........G..A..T..........CT...A..A......C...........

280
261  A   D   D   D   F   T   Y   E   R   R   K   E   S   A   A   Y   I   P   F
     GCAGATCCTGATGACTTTACCTATGAGAGGCGGAAAGAGTCGGCAGCATATATTCCATTT
     ..CAG...C..GA..........C...........G..CT..........C..G..C...C 300
281  G   Q   G   D   F   Y   H   A   A   I   F   G   G   T   P   I   Q   V   L
     GGCCAGGGGGATTTTTATTACCATGCAGCCATTTTTGGAGGAACACCGATTCAGGTTCTC
     ..AG..........................C..G........................CA...

320
301  N   I   T   Q   E   C   F   K   G   I   L   L   D   K   K   N   D   I   E   A
     AACATCACCCAGGAGTGCTTTAAGGGAATCCTCCTGGACAAGAAAAATGACATAGAAGCC
     ........AG........................G........A........C.......

340
321  E   W   H   D   E   S   H   L   N   K   Y   F   L   L   N   K   P   S   K   I
     GAGTGGCATGATGAAAGCCACCTAAACAAGTATTTCCTTCTCAACAAACCCTCTAAAATC
     C............................A..C..........T...........A....

360
341  L   S   P   E   Y   C   W   D   Y   H   I   G   L   P   S   D   I   K   T   V
     TTATCTCCAGAATACTGCTGGGATTATCATATAGGCCTGCCTTCAGATATTAAAACTGTC
     C.........G..T.............C............G.................G.

361  K   L   S   W   Q   T   K   E   Y   N   L   V   R   K   N   V   *
     AAGCTATCATGGCAAACAAGAGTATAATTTGGTTAGAAAGAATGTCTGA
     ...G..G.T.....G.............................T...
```

5,879,675

COMPOSITIONS AND METHODS FOR VACCINES COMPRISING α-GALACTOSYL EPITOPES

This is a continuation-in-part of application Ser. No. 08/213,200 filed Mar. 15, 1994, now abandoned.

FIELD OF THE INVENTION

The invention relates to cancer and viral vaccines

BACKGROUND OF THE INVENTION

The basic rationale for immune therapy against tumors is the induction of an effective immune response against tumor-associated antigens (TAA), which in turn results in immune-mediated destruction of proliferating tumor cells expressing these antigens. For an immune response to be effective against TAAs comprising protein, these antigens must first be endocytosed by macrophages. Within macrophages, TAAs are degraded in the lysosomal compartment and the resulting peptides are expressed on the surface of the macrophage cell membrane in association with MHC Class II molecules. This expression mediates recognition by specific CD4+ helper T cells and subsequent activation of these cells to effect the immune response (Stevenson, 1991, FASEB J. 5:2250; Lanzavecchia, 1993, Science 260:937; Pardoll, 1993, Immunol. Today 14:310). The majority of human TAA molecules have not been defined in molecular terms and as a consequence, no generic version of these molecules is available for exploitation as a potential anti-tumor vaccine. Attempts to modify autologous tumor cells in each individual patient as a means of eliciting an immune response to TAAs have met with little success. In order for autologous TAA-expressing tumor cells to function as effective vaccines, they must be opsonized in some manner so that their phagocytosis by macrophages is enhanced.

To date, available viral vaccines comprise either infectious, attenuated live virus, non-infectious killed virus or subunits thereof. While live attenuated virus is a more efficacious vaccine than killed virus, vaccines of this type are often genetically unstable and thus, have the potential to revert to a wild type, virulent phenotype. In addition, administration of live attenuated vaccines is contraindicated in immunocompromised individuals and in pregnant women. Non-infectious, killed virus vaccines and vaccines comprising viral subunits also have disadvantages in that they have insufficient immunogenic properties and must be administered in high concentrations at frequent intervals.

Anti-Gal, a naturally occurring antibody present in all humans, specifically interacts with the carbohydrate epitope Galα1-3Galβ1-4GlcNAc-R (α-galactosyl epitope). This antibody does not interact with any other known carbohydrate epitope produced by mammalian cells (Galili, 1993, Springer Seminar Immunopathology 15:153). Anti-Gal constitutes approximately 1% of circulating IgG (Galili et al., 1984, J. Exp. Med. 160:1519) and is also found in the form of IgA and IgM (Davine et al., 1987, Kidney Int. 31:1132; Sandrin et al., 1993, Proc. Natl. Acad. Sci. USA 90:11391). It is produced by 1% of circulating B lymphocytes (Galili et al., 1993, Blood 82:2485).

Both anti-Gal and α-galactosyl epitope exhibit a unique distribution pattern in mammals. Anti-Gal is *produced abundantly in humans, apes and Old World monkeys, but is absent in New World monkeys, prosimians and non-primate mammals (Galili et al., 1987, Proc. Natl. Acad. Sci. USA 84:1369). In contrast, the α-galactosyl epitope is found as part of the terminal carbohydrate structure on glycolipids and on carbohydrate chains of glycoproteins, in particular on asparagine (N)-linked carbohydrate chains, in non-primate mammals, prosimians and New World monkeys, but is absent in Old World monkeys, apes and humans (Galili et al., 1987, Proc. Natl. Acad. Sci. USA 84:1369; Galili et al., 1988, J. Biol. Chem. 263:17755).

Asparagine (N)-linked carbohydrate chains similar to those present on mammalian cells, are found attached to envelope glycoproteins of viruses which bud from vertebrate cells (Klenk, 1990, p. 25–37. In: Regenmortel and Neurath (ed.). Immunochemistry of Viruses, II. The Basis for Serodiagnosis and Vaccines. Elsevier Publishers B.V., N.Y.). These carbohydrate chains most often are of the simple high-mannose type containing mannose and N-acetylglucosamine only or of the complex type wherein they contain additional carbohydrates such as galactose, N-acetylglucosamine, fucose and sialic acid. Oligosaccharide chains on viral glycoproteins are synthesized in large part by host cell glycosylation enzymes (Kornfeld et al., 1985, Ann. Rev. Biochem. 54:631; Schlesinger et al., 1986, p. 121–148. In: Schlesinger and Schlesinger (ed.), The Togaviridae and Flaviviridae, Plenum Press, N.Y.; Rademacher et al., 1988, Ann. Rev. Biochem. 57:785)).

Sialylated N-linked complex carbohydrate chains are common on viral glycoproteins and on cell surface glycoproteins since sialyltransferases, which are prevalent in the Golgi apparatus of all mammalian cells, "cap" N-acetyllactosaminyl residues of viral carbohydrate chains with sialic acid (Klenk et al., 1980, Curr. Topics Microbiol. Immunol. 90:19–48; Kornfeld et al., 1985, Ann. Rev. Biochem,. 54:631; Rademacher et al., 1988, Ann. Rev. Biochem. 57:785). Geyer et al. (1984, Biochemistry 23:5628) report α-galactosyl epitopes as a major carbohydrate structure on Friend murine leukemia virus.

SUMMARY OF THE INVENTION

The invention encompasses compositions and methods for enhancing an immune response to an antigen in an anti-Gal synthesizing animal. In order to elicit an effective, protective immune response to a vaccine, the vaccinating antigen must be processed in vivo by antigen-presenting cells or macrophages. Processing includes uptake of antigen by macrophages, fragmentation of antigen within the lysosomal compartment of these cells and ultimately, presentation of the fragmented peptide on the membrane of the macrophage in association with class II major histocompatibility (MHC) molecules. According to the methods and compositions of the invention, an immune response to an antigen is enhanced by positioning α-galactosyl epitopes either on or juxtaposed to the antigen. When an antigen so treated is administered to an anti-Gal synthesizing animal, opsonization of the antigen is effected by binding of anti-Gal to the α-galactosyl epitopes thereby enhancing phagocytosis and subsequent processing of the antigen by macrophages.

In one aspect, the invention features a method of inducing an immune response to an antigen in an anti-Gal synthesizing animal comprising providing an α-galactosyl epitope containing complex, which complex includes the antigen and a lipid bilayer, and administering an immunizing effective amount of the complex to the animal.

In another aspect, the invention features a method of opsonizing an antigen in an anti-gal synthesizing animal comprising providing an α-galactosyl epitope containing complex, which complex includes the antigen and a lipid bilayer, and administering an immunizing effective amount of the complex to the animal.

In both aspects, the antigen is preferably positioned so that it is juxtaposed to the lipid bilayer. More preferably, the antigen is either inserted in or encapsulated by the lipid bilayer.

In yet another aspect, the invention features a method of opsonizing an antigen in an anti-Gal synthesizing animal comprising encapsulating the antigen in a lipid bilayer to form a complex, incubating the complex in the presence of α-galactosyl epitope containing glycosphingolipids to effect insertion of the α-galactosyl epitopes into the lipid bilayer, and administering the complex so incubated to the animal.

In another aspect, the invention features a method of opsonizing a tumor cell in an anti-Gal synthesizing animal having a tumor comprising obtaining the tumor cell from the animal, incubating the cell in the presence of a preparation of α-galactosyl containing glycosphingolipids to effect insertion of the α-galactosyl epitopes into the membrane of the cell, irradiating the cell so treated and then administering the cell to the animal.

In yet another aspect, the invention features a method of opsonizing a tumor associated antigen in an anti-Gal synthesizing animal having a tumor comprising obtaining a tumor associated antigen containing cell from the animal, extracting the cell membrane of the cell, incubating the cell membrane in the presence of α-galactosyl epitope containing glycosphingolipids to effect insertion of the α-galactosyl epitopes into the membrane and administering the cell membrane so treated to the animal.

The invention includes yet another method of opsonizing a tumor associated antigen in an anti-Gal synthesizing animal having a tumor comprising obtaining a tumor associated antigen containing cell from the animal, incubating the cell in the presence of neuraminidase, further incubating the cell in the presence of α1,3 galactosyltransferase and UDP-galactose to effect addition of α-galactosyl epitopes to the tumor associated antigens, irradiating the cell so incubated and administering the cell to the animal.

In yet another aspect, the invention includes a method of opsonizing a tumor associated antigen in an anti-Gal synthesizing animal having a tumor comprising obtaining a tumor associated antigen containing cell from the animal, extracting the cell membrane from the cell, incubating the cell membrane in the presence of neuraminidase, further incubating the cell membrane in the presence of α1,3 galactosyltransferase and UDP-galactose to effect addition of α-galactosyl epitopes to the tumor associated antigen and administering the cell membrane so incubated to the animal.

Also included in the invention is an α-galactosyl epitope containing tumor cell of an anti-Gal synthesizing animal.

The invention further includes a method of opsonizing a glycoprotein containing virus in an anti-Gal synthesizing animal comprising propagating the virus in an α-galactosyl epitope containing cell to effect addition of α-galactosyl epitopes to the virus, separating the virus so propagated from the cell, suspending the separated virus in pharmaceutically acceptable carrier and administering the virus to the animal.

In yet another aspect, the invention includes a method of opsonizing a glycoprotein containing virus in an anti-Gal synthesizing animal, wherein the glycoprotein has at its carbohydrate terminus a sialic acid residue. The method comprises incubating the virus in the presence of neuraminidase, further incubating the virus in the presence of α1,3 galactosyltransferase and UDP-galactose to effect addition of α-galactosyl epitopes to the glycoprotein, purifying the virus so incubated, suspending it in a pharmaceutically acceptable carrier, and administering the virus to the animal.

In a further aspect, the invention includes a method of opsonizing a non-sialic acid containing glycoprotein containing virus in an anti-Gal synthesizing animal comprising incubating the virus in the presence of α1,3 galactosyltransferase and UDP-galactose to effect addition of α-galactosyl epitopes to the glycoprotein, purifying the virus so incubated, suspending the virus in a pharmaceutically acceptable carrier and administering the virus to the animal.

In yet another aspect, the invention features a viral vaccine effective in an anti-Gal synthesizing animal comprising an immunizing effective amount of an α-galactosyl epitope containing virus, or a viral subunit, suspended in a pharmaceutically acceptable carrier.

In preferred embodiments, the tumor is a leukemia, lymphoma, myeloma, melanoma, ovarian carcinoma, lung carcinoma, mammary carcinoma, thyroid carcinoma, colon carcinoma or sarcoma. More preferably, the tumor is leukemia.

In yet other preferred embodiments, the animal is a bird, an Old World monkey or a human, and more preferably, the animal is a human.

In yet more preferred embodiments, the antigen is a component of an infectious agent belonging to the group consisting of a virus, a bacterium, a parasite and a yeast. More preferably, the virus is a member of the following virus families: Orthomyxoviruses, Rhabdoviruses, Hepadnaviruses, Togaviruses, Bunyaviruses, Retroviruses, Paramyxoviruses, Flaviviruses, Herpesviruses, Arenaviruses, or Reoviruses. Even more preferably, the virus is an influenza virus, a rabies virus, a human immunodeficiency virus, a hepatitis B virus, an eastern, western or Venezuelan equine encephalitis virus, a Japanese encephalitis virus, a tick-borne encephalitis virus, a Russian springsummer encephalitis virus or a Rift Valley fever virus. Most preferably, the virus is influenza virus or eastern equine encephalitis virus and the antigen is influenza virus hemagglutinin or eastern equine encephalitis virus E1 or E2 glycoprotein, or glycoproteins of human immunodeficiency virus.

The invention should also be construed to include other carbohydrates capable of binding to anti-Gal to effect opsonization of an antigen according to the methods of the invention. For example, melibiose and like carbohydrates may bind anti-Gal to effect opsonization. The invention further includes synthetic α-galactosyl epitopes and like carbohydrate structures and also includes synthetic or naturally occurring glycolipids other than GSLs which contain α-galactosyl epitopes capable of interacting with anti-Gal.

By antigen is meant any antigen whose presence in an animal is associated with a disease state, including but not limited to, tumor associated antigens and viral, bacterial, parasitic and fungal antigens. Also included in the term virus are whole infectious organisms or subunits thereof.

By subunit is meant a portion of a virus or antigen which is itself antigenic, i.e., capable of inducing an immune response in an animal. The term should be construed to include subunits which are obtained by both recombinant and biochemical methods.

By tumor cell is meant a cell which is a component of a tumor in an animal, or a cell which is determined to be destined to become a component of a tumor, i.e., a cell which is a component of a precancerous lesion in an animal.

The term tumor associated antigen (TAA) includes all antigens associated with a tumor in an animal, including the traditionally named TAAs.

By opsonization of an antigen is meant binding of the antigen by anti-Gal thereby effecting enhanced phagocytosis and subsequent MHC-associated expression of the antigen by macrophages in the presence of α-galactosyl galactosyl epitopes compared with phagocytosis and expression of the antigen by macrophages in the absence of α-galactosyl epitopes.

By anti-Gal synthesizing animal is meant an animal which naturally expresses IgG, IgA or IgM anti-Gal antibody.

The term animal should be construed to include all anti-Gal synthesizing animals including those which are not yet known to synthesize anti-Gal. For example, some animals such as those of the avian species, are known not to synthesize α-galactosyl epitopes. Due to the unique reciprocal relationship among animals which synthesize either anti-Gal or α-galactosyl epitopes, it is believed that many animals heretofore untested in which α-galactosyl epitopes are absent may prove to be anti-Gal synthesizing animals. The invention also encompasses these animals.

By immunizing effective amount is meant an amount of antigen which elicits an immune response when administered to an anti-Gal synthesizing animal.

By juxtaposed to is meant that the antigen and α-galactosyl galactosyl epitope are positioned near each other such that upon binding to anti-Gal they are together phagocytosed by a single macrophage. This term should also be construed to include (i) encapsulation of antigen by a lipid bilayer, (ii) micelle-like structures comprising lipid bilayer and antigen, wherein either the lipid bilayer or antigen has attached thereto α-galactosyl epitopes, and (iii) whole cells or membrane fragments.

BRIEF DESCRIPTION OF THE FIGURES

FIG. 5 is a graphical representation of the number of anti-Gal molecules bound to GSL-treated cells. GSL-treated cells (open columns) untreated cells (closed columns) were incubated in the presence of anti-Gal and subsequently with $^{125}$I protein A. The number of anti-Gal molecules per cell (in parentheses) was assessed from the amount of radioactivity bound to the cells.

FIG. 7 is a graph of a radioimmunoassay depicting binding of anti-Gal to bovine thyroglobulin (○), $EEE_{3T3}$ (□), and $EEE_{vero}$ (Δ).

FIG. 9. Nucleotide (SEQ ID NO:1) and deduced amino acid sequence (SEQ ID NO:2) of marmoset α1,3GT cDNA (top), and comparison with murine α1,3GT DNA (bottom, SEQ ID NO:3). The transmembrane region is underlined. Dots represent nucleotides in murine DNA which are identical to marmoset DNA. Dashed lines indicate nucleotides which are absent in murine DNA compared with marmoset DNA.

inactivated PR8$_{MDBK}$ virus (lane 2); PR8$_{MDCK}$ virus (lane 3); and PR8$_{egg}$ virus (lane 4).

Figure 14C:
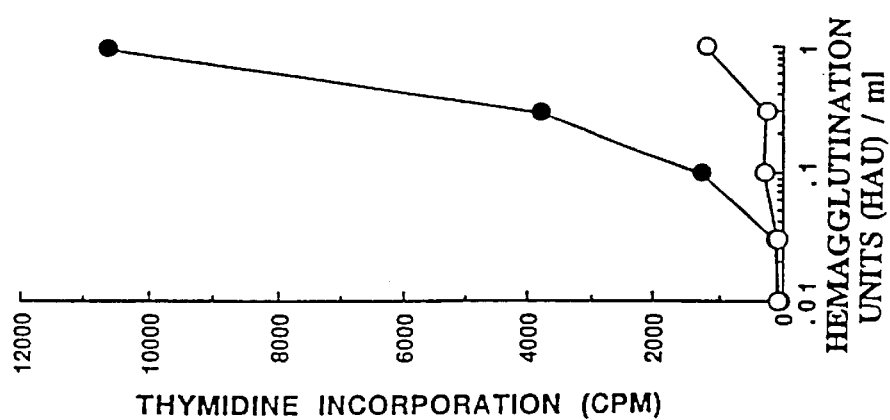
Figure 14B:
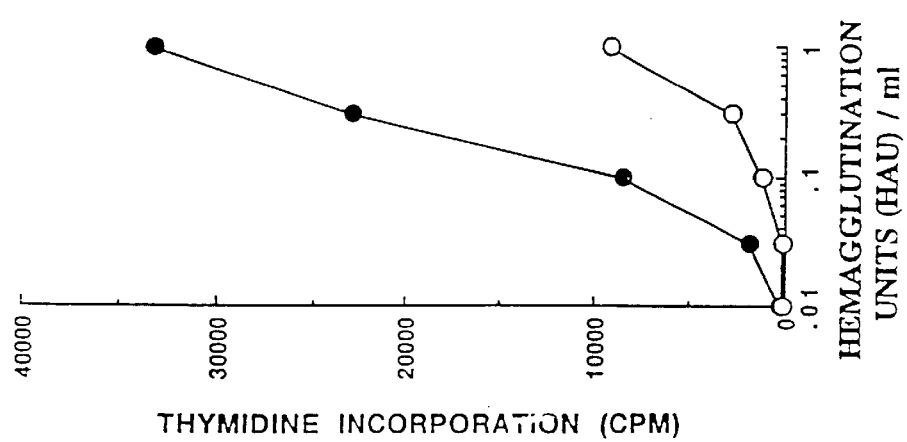
Figure 14A:
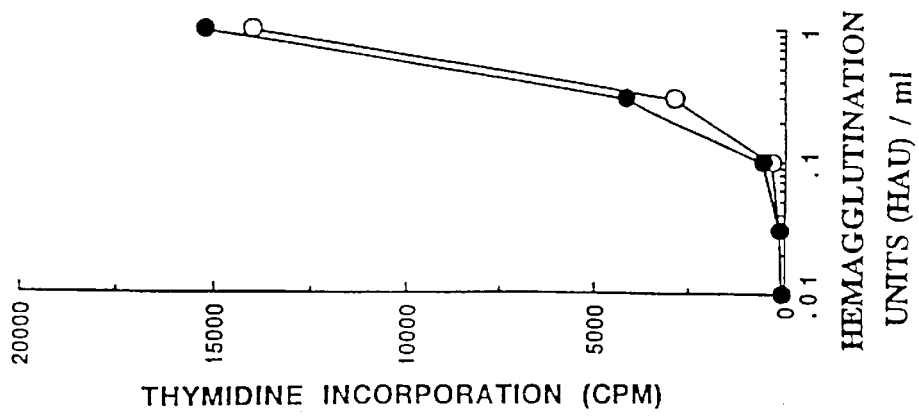

FIGS. 14A, 14B and 14C are plots showing the effect of anti-Gal on the presentation of HA antigenic peptides from inactivated PR8$_{egg}$ virus (14A), PR8$_{MDBX}$ virus (14B), and PR8$_{MDCK}$ virus (14C) by splenic irradiated APC. The presentation was measured by the proliferative response of HA specific T$_H$ cells. ○, virus without anti-Gal; ●, virus pre-incubated with anti-Gal. Virus concentration corresponds hemagglutination units per ml (HAU/ml) prior to the inactivation with formalin.

Figure 15:
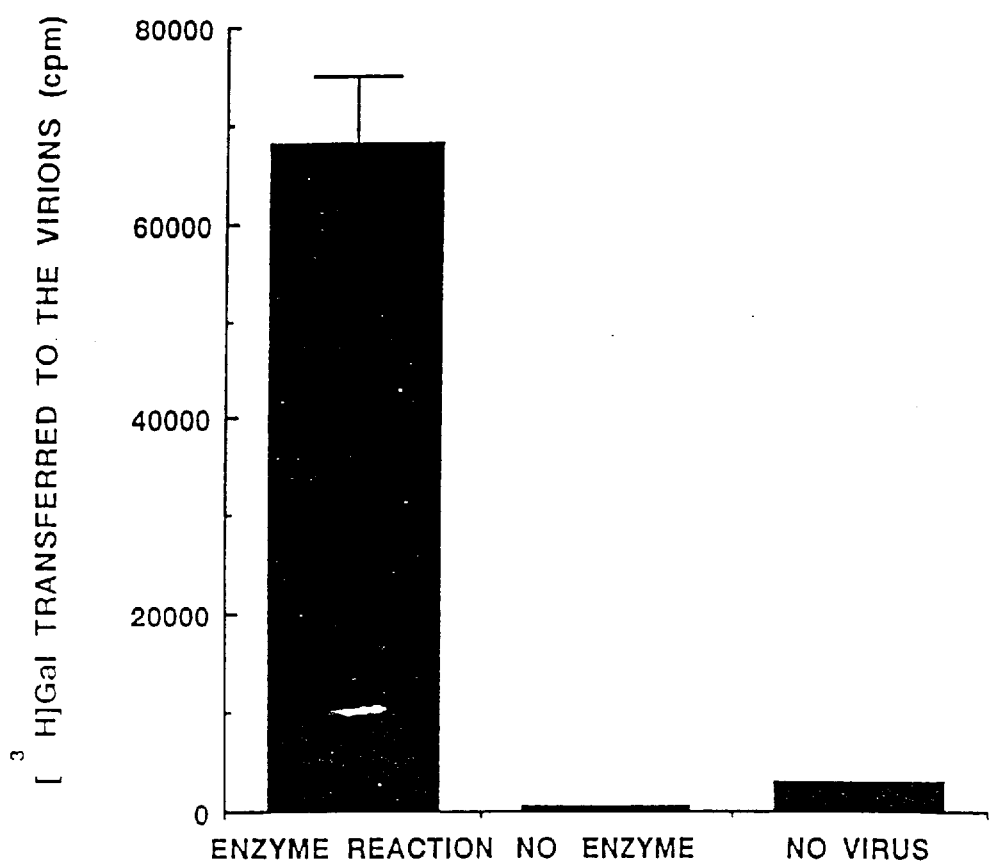

FIG. 15 ("ENZYME REACTION") shows the transfer of [$^3$H]Gal from UDP-[$^3$H]Gal to influenza virus by recombinant (rec.) marmoset α1,3GT. Controls of absence of enzyme ("NO ENZYME"), and absence of virus in the enzyme reaction ("NO VIRUS"), are included. The data represent the mean±S.E. of three experiments.

Figure 16A:
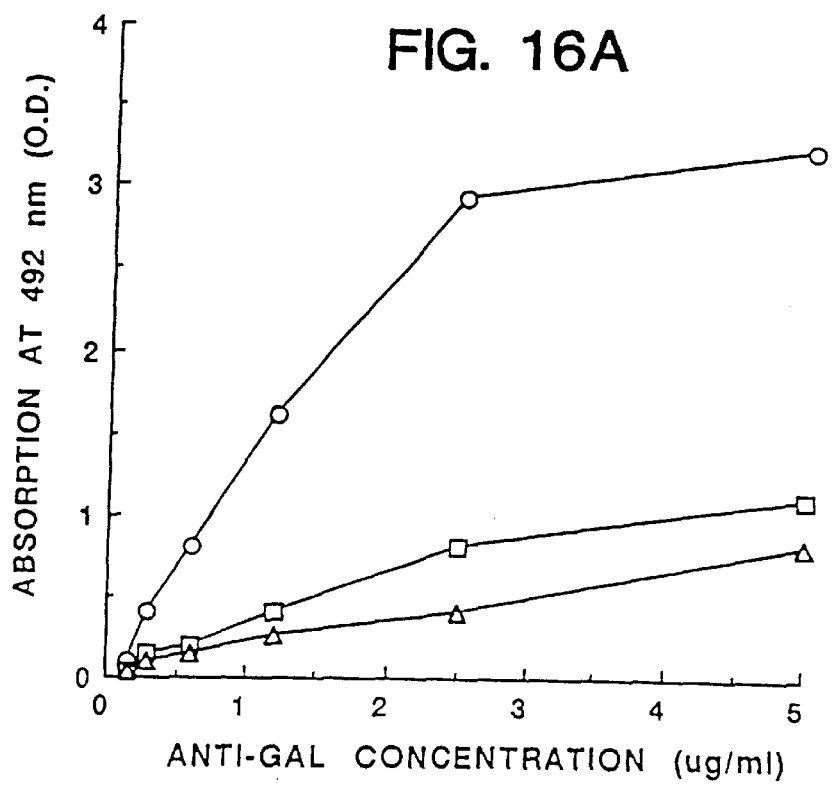
Figure 16B:
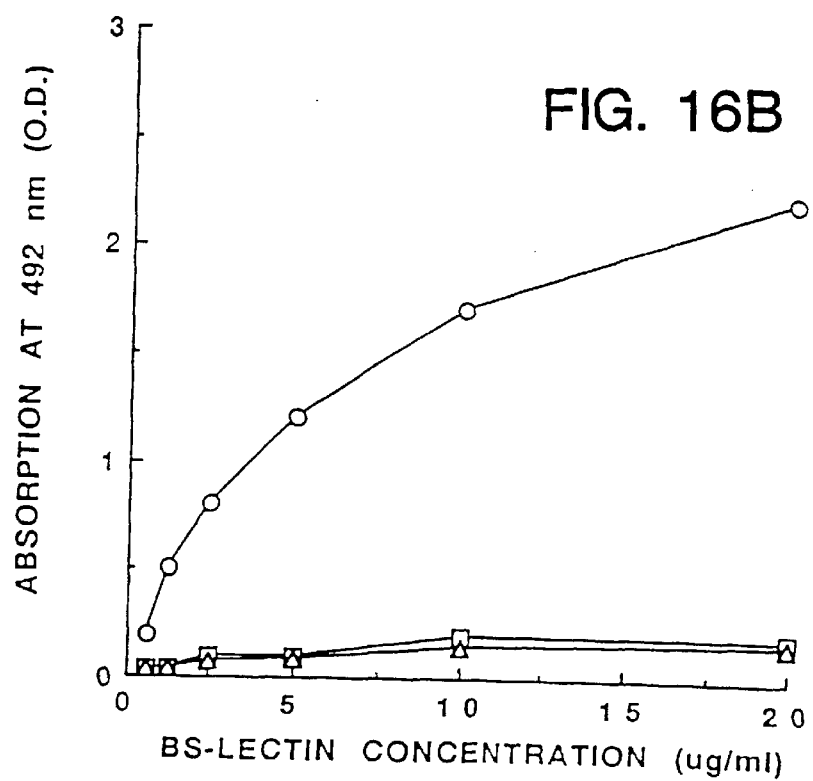

FIGS. 16A and 16B are plots of the binding of biotinylated anti-Gal (16A), or biotinylated BS-lectin (16B) to various influenza virus preparations in ELISA. (○)—virus subjected to α-galactosyl epitope synthesis by rec. α1,3GT; (□)—virus incubated with α1,3GT but in absence of UDP-Gal, so α-galactosyl epitopes could not be synthesized; (Δ) original untreated virus.

Figure 17:
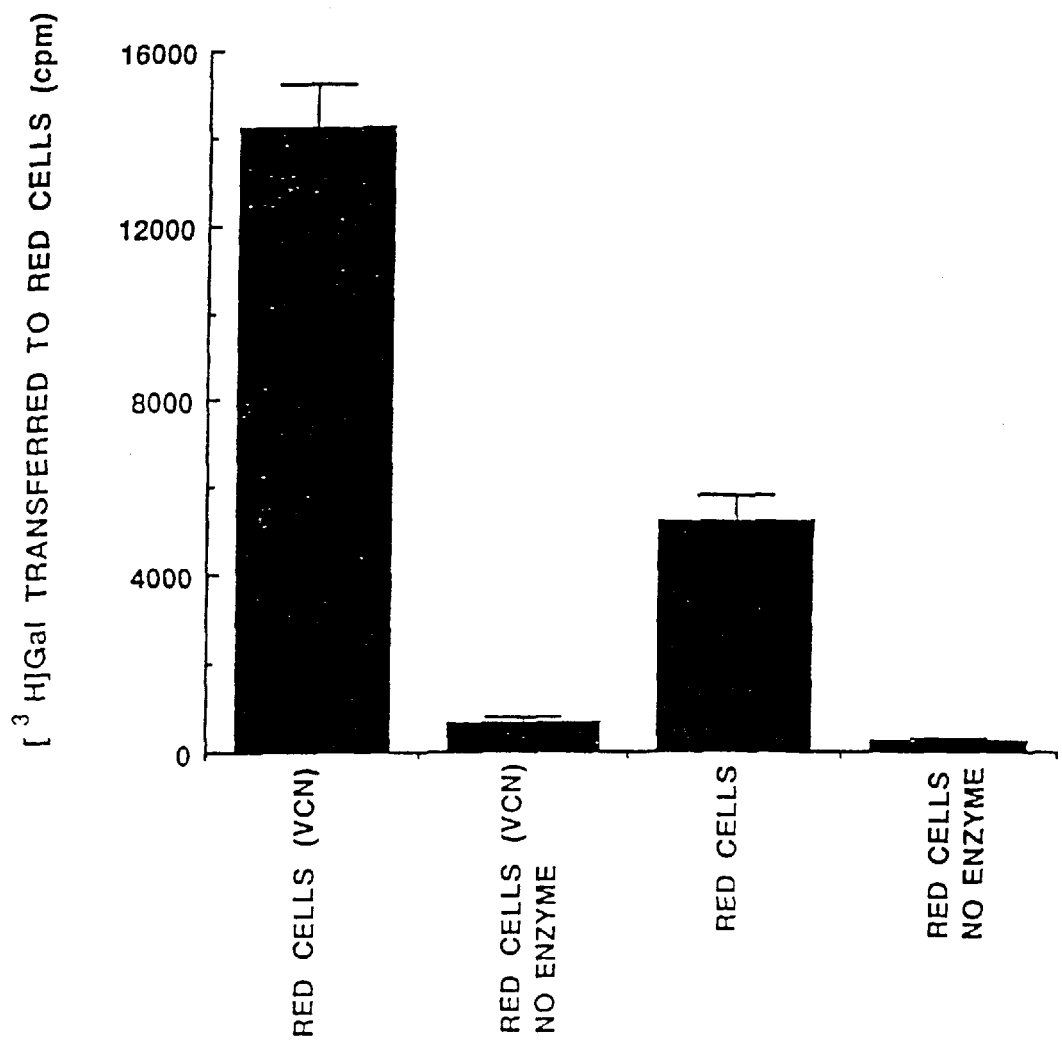

FIG. 17 shows the transfer of [$^3$H]Gal from UDP-[$^3$H]Gal to 10$^7$ human red cells ("RED CELLS"), or 10$^7$ human red cells treated with Vibrio cholera neuraminidase ("RED CELLS (VCN)"). Controls (no enzyme) represent the non-specific retention of UDP-[$^3$H]Gal following harvesting of the red cells. Note that following VCN treatment many more N-acetyllactosamine residues are available for transfer of [$^3$H]Gal. The data represent the mean±S.E. of three experiments.

Figure 18:
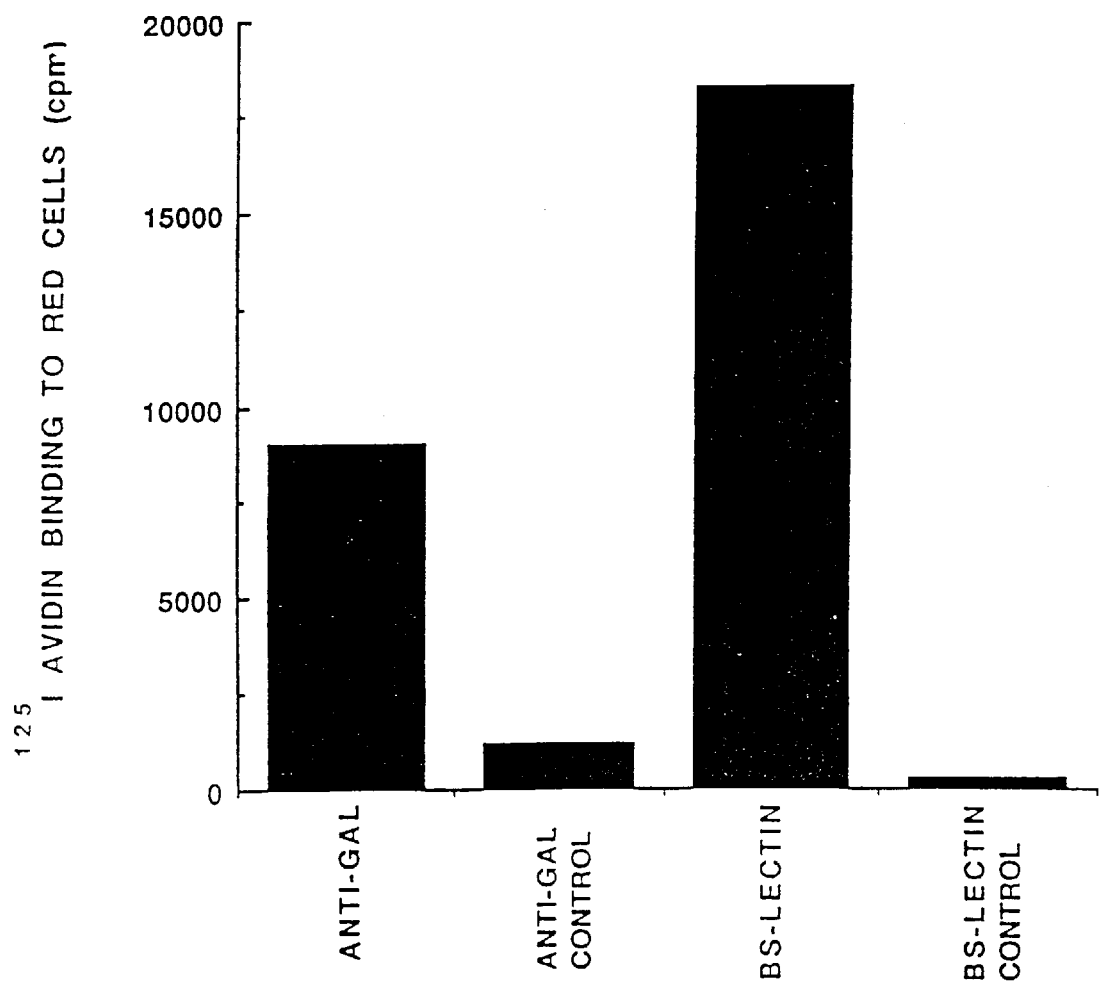

FIG. 18 shows the binding of biotinylated anti-Gal (5 μg/ml), or biotinylated BS lectin (20 μg/ml) to 10$^7$ human red cells with de novo synthesized α-galactosyl epitopes, as assessed by subsequent binding of $^{125}$I-avidin. Controls represent 10$^7$ VCN-treated red cells which were not subjected to α1,3GT activity. The data represent the mean of two experiments.

Figure 19A:
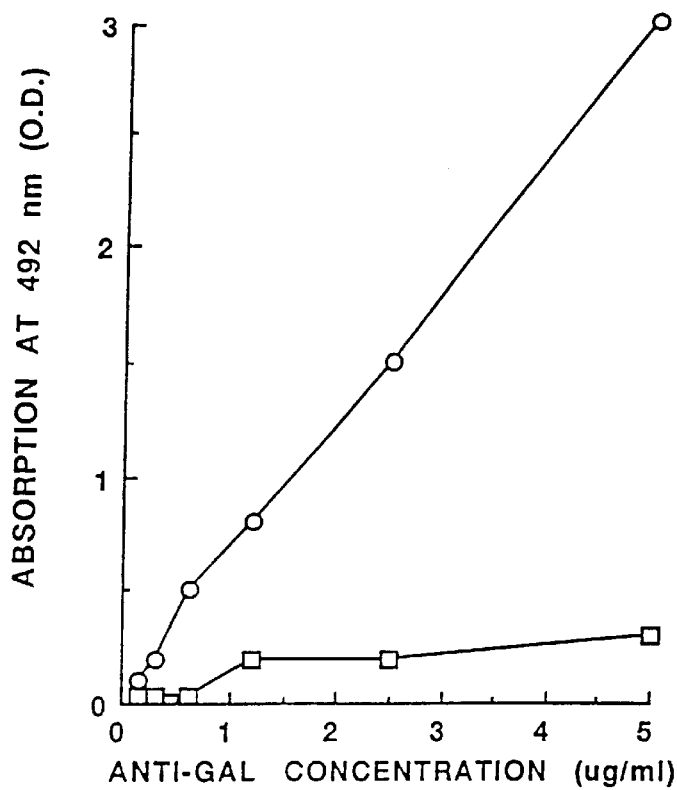
Figure 19B:
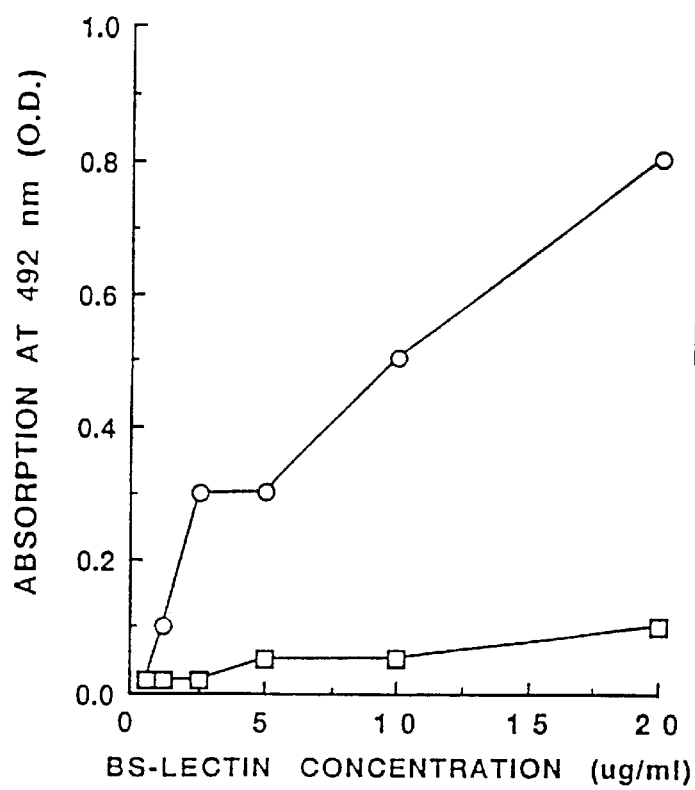

FIG. 19A and 19B are plots of the binding of biotinylated anti-Gal (19A), or biotinylated BS-lectin (19B) to human red cells with α-galactosyl epitopes (○), or to control VCN-treated red cells (□), in ELISA.

DETAILED DESCRIPTION OF THE INVENTION

In order to effectively opsonize TAAs or viral antigens or any other antigen according to the methods of the invention, α-galactosyl epitopes must first be positioned either onto membranes containing the antigens to be opsonized or onto the antigens themselves. This can be accomplished using three basic methods. The first involves extraction of α-galactosyl epitope containing GSLs from a GSL-rich source, such as but not limited to rabbit red blood cell membranes, followed by incubation of GSLs with a membrane preparation containing the subject antigen to effect insertion of the GSLs into the membrane. In this case, α-galactosyl epitopes present on GSLs are not physically transferred onto the antigen. Rather, epitopes attached to GSLs are dispersed among molecules of antigen also embedded within the membrane, or epitopes attached to GSLs are dispersed in a membrane preparation which membrane contains the test antigen enclosed within it. Binding of anti-Gal to the epitopes so inserted induces phagocytosis by macrophages of the membrane, and therefore the antigen associated therewith, resulting in efficient processing and subsequent expression of the antigen.

In the second method, α-galactosyl epitopes are added directly to the carbohydrate moiety of the antigen of choice by means of a biochemical reaction using the enzyme α1,3 galactosyltransferase (α1,3GT) This enzyme catalyzes the following reaction:

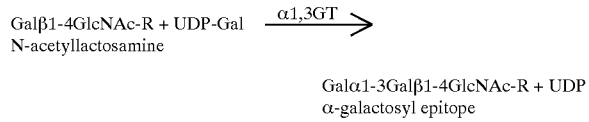

Galα1-3Galβ1-4GlcNAc-R + UDP
α-galactosyl epitope (Basu et al., 1973, J. Biol. Chem. 248:12700; Elices et al.; 1986, J. Biol. Chem. 261:6064; Blanken et al., 1985, J. Biol. Chem. 260:12927). Recombinant α1,3GT which may be used in the reaction has been obtained from several different species including the New World monkey, the marmoset (described below). In order for α-galactosyl epitopes to be successfully added to an antigen, terminal sialic acid residues if present, must first be removed. This is easily accomplished using the enzyme neuraminidase.

In the third method, cells known to express α-galactosyl epitopes serve as hosts for virus replication. Viruses so replicated thus contain α-galactosyl epitopes attached to their glycoproteins. This method is applicable to all viruses and other intracellular parasites which acquire α-galactosyl epitopes during replication in α-galactosyl epitope synthesizing cells.

Membrane preparations include whole tumor cells or membrane fractions thereof, complete virus particles, fractions of viral envelopes or viral subunits embedded in a lipid bilayer such as a liposome. Membrane preparations also include natural or artificial membranes into which antigens are inserted, or natural or artificial membranes which contain antigens associated therewith, for example, wherein the membrane actually encapsulates the antigen. An antigen may be encapsulated within a membrane by sonication of a mixture of membrane and antigen. Alternatively, the antigen may be inserted directly into the membrane provided it contains a membrane insertion signal. Such a membrane insertion signal may be naturally present as a component of the antigen, or it may be engineered to be an integral component of the antigen using recombinant techniques known to those of skill in the art. In addition, membrane preparations which have antigen associated with them, which antigen is neither encapsulated nor inserted into the membrane may also be useful. Such preparations usually comprise micelletype arrangements of antigen and membrane formed as a result of mixing preparations of membrane and antigen. Preparations of membranes also include resealed red blood cell membranes derived from lysed cells (ghosts), which membranes may contain α-galactosyl epitopes.

When whole cells are used as membrane antigen preparations, the cells are irradiated such that they are rendered non-viable prior to administration to the animal. Irradiation is accomplished using X-rays or gamma rays at a cell-killing dose, which dose depends upon the type and number of cells and which will be readily apparent to a skilled artisan.

Viral subunits may be obtained from virions using biochemical methods or they can be expressed by recombinant means in suitable eukaryotic cells. Methods of expressing viral subunits are common in the art which methods may vary according to the type of virus used. For example, methods of expressing viral subunits are described in the following articles and in the references cited therein: Possee, 1986, Virus research 5:43; Kuroda et al., 1986, EMBO J. 5: 1359; Doerfler, 1986, Curr. Topics Microbiol. Immunol. 131:51; Rigby, 1983, J. Gen. Virol. 64:255; Mackett et al., 1985, In: DNA Cloning, A Practical Approach, Vol II, Ed. D. M. Glover, IRL Press, Washington, D.C.; Rothestein, 1985, In: DNA Cloning, A Practical Approach, Supra; Kinney et al., 1988, J. Gen. Virol. 69:3005; Panical et al., 1983, Proc. Natl. Acad. Sci. USA 80:5364; Small et al., 1985, In: Vaccinia Viruses as Vectors for Vaccine Antigens, pp. 175–178, Ed. J. Quinnan, Elsevier, N.Y.

Suitable eukaryotic cells include avian and mammalian cells which synthesize α-galactosyl epitopes or which can be biochemically altered such that they serve as acceptors for such epitopes. Yeast cells may also be used provided the subject carbohydrate structures are also altered biochemically to accept α-galactosyl epitopes (Robbins et al., 1977, Cell 12:893).

To opsonize tumor cells and thereby enhance their phagocytosis by macrophages, methods have been developed which position α-galactosyl epitopes on tumor cells. Cells so treated are capable of binding anti-Gal, which binding promotes phagocytosis by macrophages. Cells, or membrane fractions obtained therefrom, of any tumor may be opsonized according to the methods of the invention. Such tumors include but are not limited to leukemias; lymphomas; myeloma; melanoma; carcinomas including ovarian, lung, mammary, thyroid and colon carcinoma; and, sarcomas. Following the addition of α-galactosyl epitopes to tumor cells, the cells are irradiated or are killed by any other means prior to re-administration to the patient.

The invention is not limited solely to use of autologous tumor cells. Rather, suitably treated allogeneic tumor cells may also be useful as tumor vaccines. Such cells may be prepared according to the methods described in Morton et al. and in Mitchell et al. (both published in Specific Immunotherapy of Cancer with Vaccines, 1993, Bystran et al., eds. New York Academy of Sciences, NY, pp. 120 and 153, respectively).

Also included in the invention are all known and as yet unidentified viruses as candidate vaccines in that it is possible to opsonize any virus or subunit thereof according to the methods of the invention. For example, for those viruses which contain glycoproteins as a component of the virion, α-galactosyl epitopes may be added directly to the glycoproteins by propagation of virus in cells synthesizing such epitopes or by direct biochemical addition using α1,3GT. Alternatively, whole virus or viral subunits, either with or without glycoprotein moieties, may be encapsulated in or positioned juxtaposed to membrane containing particles which particles have α-galactosyl epitopes capable of binding anti-Gal, thus inducing phagocytosis by macrophages. Furthermore, there exists viruses without envelopes which viruses contain complex carbohydrates onto which α-galactosyl epitopes may be added. Moreover, it is possible to render viral subunits which do not naturally contain membrane insertion signals capable of being inserted into a lipid bilayer by genetic engineering. Such techniques are common in the art and are described for example in Sambrook et al., (1989, Molecular Cloning, A Laboratory Manual, Cold Spring Harbor, N.Y.) and in Masilbay et al. (1993, J. Biol. Chem. 268:9908). Alternatively, subunits may be linked by biochemical techniques to hydrophobic moieties which may themselves be inserted into a membrane.

Viruses for which vaccines are currently available and whose efficacy can be improved according to the methods of the invention include influenza virus (Orthomyxovirus); rabies virus (Rhabdovirus); hepatitis B virus (Hepadnavirus); eastern, western and Venezuelan equine encephalitis virus (Togavirus/Alphavirus genus); and, Japanese encephalitis virus, tick-borne encephalitis virus and Russian spring-summer encephalitis virus (Flavivirus); Rift Valley fever virus (Bunyavirus) reviewed in Melnick (1985) In: High Technology Route to Virus Vaccines Ed. Dreesman, Bronson and Kennedy, American Society for Microbiology, Washington, D.C.) and in Ogra et al. (1990, Prog. Med. Virol. 37:156). Viruses for which vaccines are not yet commercially available but which may also be useful when treated according to the methods of the invention include, but are not limited to human immunodeficiency and human T-cell leukemia viruses (Retrovirus); respiratory syncytial virus and other paramyxoviruses (Paramyxovirus); herpes simplex viruses types 1 and 2, varicella zoster virus, cytomegalovirus and other herpes viruses (Herpesviruses); dengue virus and Saint Louis encephalitis virus (Flavivirus); hantaan virus (Bunyavirus); Lassa virus (Arenavirus); and, rotavirus (Reovirus). In addition, there exist viral vaccines comprising live attenuated viruses the administration of which to humans is associated with some measure of risk of mild to severe side effects. It is now possible according to the methods of the invention to enhance the immunogenicity of killed virus vaccines which may serve to reduce the use of their live, more risk-associated counterparts. Thus, vaccines which currently comprise live virus such as measles virus, mumps virus, rubellavirus etc. are all encompassed by the invention.

Antigens which can be opsonized according to the methods of the invention therefore encompass all antigens whose phagocytosis by macrophages is enhanced because of the addition of α-galactosyl epitopes either directly thereon or because of their juxtaposition to such epitopes.

Vaccines are prepared by suspension of a suitable concentration of α-galactosyl epitope containing antigen in a pharmaceutically acceptable carrier. The composition of the carrier will depend upon the type of vaccine and the route of administration and will be readily apparent to one skilled in the art. The vaccine may be administered in a dose of $10^2$ to $10^9$ cells per dose (in the case of whole cells) or a similar equivalent of cell membranes. In the case of viral vaccines, virus may be administered in dose ranging from 1 µg to 50 mg of virus per dose, or a similar equivalent of subunit. Determination of the appropriate dosage of vaccine will be apparent to one of skill in the art and will depend upon the antigens comprising the vaccine, the age of the patient and their general and immunological health. In the case of tumor vaccines, dosage will also depend upon the severity and type of tumor to be treated and may be determined empirically for each individual patient. Unless patients with tumors are severely immunocompromised it has been discovered that their levels of circulating anti-Gal are normal.

In order to improve the efficacy of tumor and viral vaccines prepared according to the methods of the invention, patients may be pretreated with adjuvant at the site of vaccination several days prior to administration of vaccine. Pretreatment with adjuvant serves to induce migration of macrophages to the site of inoculation, thereby enhancing the rate of phagocytosis of opsonized antigens. Alternatively and particularly in the case of viral vaccines, patients may be treated with adjuvant and vaccine simultaneously. Adjuvants suitable for this purpose include aluminum hydroxide and like adjuvants.

Vaccines are administered to a mammal, particularly a human, either subcutaneously, intramuscularly, orally, intravenously, intradermally, intranasally and intravaginally. Prior to oral administration, the vaccine is first mixed with a solution containing a sufficient amount of sodium bicarbonate or other suitable compound capable of neutralizing stomach acid (approximately 2 grams). Alternatively, the vaccine usually in lyophilized form, can be formulated as tablets which tablets are treated with a coating capable of resisting stomach acid. There will now be described experimental details for the practice of the invention. The examples given below relate to but are not limited to opsonization of tumor cells and viruses. As will be evident from the data presented, the methods of the invention are applicable to opsonization of any vaccine-candidate antigen.

Isolation and biotinylation of anti-Gal. Anti-Gal was isolated from normal blood group AB sera by affinity chromatography on synthetic Galα1-3Galβ1-4GlcNAc-R linked to Synsorb beads (Synsorb 115, Chembiomed, Edmonton, Alberta, Canada) (Galili et al., 1987, J. Exp. Med. 165:693; Galili et al., 1987, Proc. Natl. Acad. Sci. USA 84:1369; Galili et al., 1988, J. Biol. Chem. 263:17755). Briefly, 100 ml batches of pooled, heat-inactivated AB human plasma were loaded onto a column containing 10 ml of Synsorb 115 beads. The column was washed at 37° C. with phosphate buffered saline (PBS) prewarmed to 37° C. An amount (0.3M) of α-methylgalactoside (Sigma) was applied to the column which was then incubated for 12 hours at 37° C. to allow for specific elution of anti-Gal. The eluate was collected and dialyzed at 4° C. against 4 liters of PBS in order to remove α-methylgalactoside. The dialysis buffer was changed every 24 hours for 4 days. The concentration of anti-Gal was measured by spectroscopy at 280 nm and antibody activity was assessed in a hemagglutination assay using rabbit red blood cells (Galili et al., 1985, J. Exp. Med. 162:573).

An aliquot of antibody at a concentration of 100 µg/ml in PBS, pH 7.4, was subjected to biotinylation as follows. N-hydroxysuccinimide-LC-biotin (Pierce, Rockford, Ill.) was added to the anti-Gal preparation at a final concentration of 3 mg/ml. The mixture was incubated for an initial 2 hours at room temperature followed by overnight at 4° C. After additional dialysis to remove free biotin, biotinylated anti-Gal was re-chromatographed on a Galα1-3Galβ1-4GlcNAc-R Synsorb column, eluted with α-galactosylmethylgalactoside and dialyzed as described above. Both biotinylated and nonbiotinylated anti-Gal preparations were stored at 20° C. in PBS containing 1% BSA.

Figure 1:
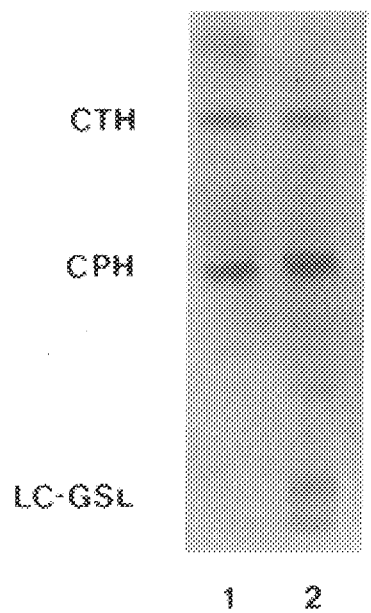
FIG. 1 is a photograph depicting isolation of rabbit GSLs (glycosphingolipids) enriched for ceramide pentahexoside (CPH) and long chain (LC) GSLS. Lane 1—GSL in the lower organic phase; Lane 2—GSL in the upper aqueous phase. Both fractions contain CPH and ceramide trihexoside (CTH). However, the relative proportion of CPH in the aqueous phase is higher than that of CTH. In addition, LC-GSLs partition exclusively to the upper aqueous phase.

Isolation of GSLs. Both rabbit and bovine red blood cell membranes are rich sources of α-galactosyl epitopes (Galili et al., 1987, Proc. Natl. Acad. Sci. USA 84:1369; Chien et al., 1979, J. Lipid Res. 20:669). The GSLs of rabbit red blood cell membranes comprise CPH having the structure Galα1-3Galβ1-4GlcNAcβ1-4Galβ1-4Glc-Cer, and CTH having the structure Galα1-4Galβ1-4Glc-Cer (FIG. 1) (Eto et al., 1968, J. Biochem. (Tokyo) 64:205; Stellner et al., 1973, Arch. Biochem. Biophys. 133:464). In addition, rabbit red blood cell membranes contain GSL molecules with longer linear or branched carbohydrate chains which also have terminal α-galactosyl epitopes (Honma et al., 1981, J. Biochem. (Tokyo) 90:1187; Egge et al., 1985, J. Biol. Chem. 260:4927). Thus, both CPH and long chain GSLs contain terminal α-galactosyl epitopes and readily interact with anti-Gal (Galili et al., 1987, J. Exp. Med. 165:593; Galili et al., 1987, Proc. Natl. Acad. Sci. USA 84:1369).

To isolate GSLs containing the α-galactosyl epitope, total lipid was extracted from membranes obtained from rabbit red blood cells using a ten-fold volume of chloroform:methanol (2:1 vol:vol). Nonsoluble material was removed from the extract by paper filtration. While constantly stirring, water was added in a volume corresponding to 25% of the volume of the extract. The mixture was held at 4° C. whereupon the components of the mixture separated into two phases, an upper aqueous phase comprising approximately 70% of the total volume and a lower organic phase comprising 30% of the total volume. The approximate relative proportions of chloroform, methanol and water in the upper phase are 3:48:47 by volume, and those in the lower phase are 86:14:1. Hydrophobic phospholipids are known to be retained in the lower organic phase (Floch et al., 1957, J. Biol. Chem. 226:497) while GSLs partition between the two phases. The organic solvents were removed from the upper phase using a rotary evaporator and the remaining solution was lyophilized, dissolved in water and dialyzed to remove salts. The suspension was again lyophilized, dissolved in a mixture of chloroform, methanol and water [30:65:8 (vol:vol)] and then chromatographed through a DEAE sephadex column to remove gangliosides (Galili et al., 1987, Proc. Natl. Acad. Sci. USA 84:1369).

GSLs which contain high amounts of carbohydrates are less hydrophobic than GSLs which contain low amounts of carbohydrates. Thus, GSLs comprising five or more carbohydrates preferentially partition to the upper aqueous phase in the experiment described above. This is evident in FIG. 1 in which GSLs obtained from the lower phase (lane 1) and upper phase (lane 2) were separated by thin layer chromatography (TLC) and subsequently stained with orcinol. It is apparent that there is more CPH in the upper phase compared with CTH and that the upper phase contains long chain (LC) GSLs which are absent from the lower phase.

GSLs extracted from the upper phase were dissolved in phosphate buffered saline to a final concentration of approximately 1 mg/ml. The mixture was sonicated using a Branson sonifier probe until the suspension became clear. The concentration of α-galactosyl epitopes on GSLs in the resulting suspension was 2 mM when assessed by radioimmunoassay (Thall et al., 1990, Biochemistry 29:3959). Approximately 70 nmoles of α-galactosyl epitopes are obtained from 1 liter of rabbit red cells using the procedures described above.

Figure 2:
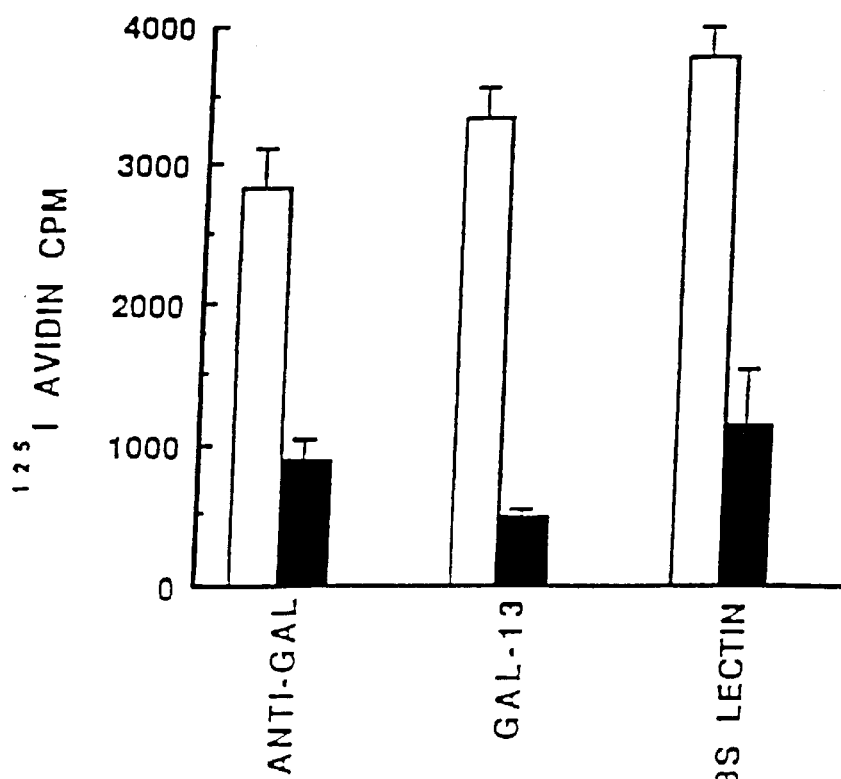
FIG. 2 is a graphical representation of the insertion of α-galactosyl epitope containing GSLs into cell membranes. Cells ($1 \times 10^7$/ml) were incubated in MEM in the presence of 0.2 mg/ml GSL for 2 hours at 37° C. Untreated cells served as a control. Unbound GSLs were removed by washing and biotinylated anti-Gal, Gal-13 or BS lectin (each at a concentration of 20 μg/ml) were individually added to aliquots of the cells and incubation was continued for 2 hours at room temperature. Next, the cells were incubated for 1 hour in the presence of $^{125}$I-avidin. Unbound avidin was removed and the amount of radioactivity associated with the cells was assessed in a gamma counter. Open columns—cells containing GSLs; closed columns—untreated cells. The results are the mean±the standard deviation, of five separate experiments.

Insertion of GSLs into membranes. To insert GSLs comprising α-galactosyl epitopes into cell membranes, 0.1 ml of the GSL suspension was added to 10×10$^6$ cells suspended in 0.4 ml minimal essential medium (MEM). The cells were incubated at 37° C. for 120 minutes with occasional stirring and were then washed three times with MEM. The presence of the inserted GSL molecules was assayed using human anti-Gal, the monoclonal antibody Gal-13, or the lectin *Bandeiraea simplicifolia* IB4 (BS lectin), each of which specifically interacts with the α-galactosyl epitope (Galili et al., 1985, J. Exp. Med. 162:573; Galili et al., 1987, J. Biol. Chem. 262:4683; Wood et al., 1979, Arch. Biochem. Biophys. 198:1). The results are shown in FIG. 2. Raji cells (a human lymphoid cell line) incubated in the absence of GSLs bound antibody and lectin at basal non-specific levels. However, cells which were incubated in the presence of GSLs bound both human anti-Gal and Gal-13 antibody, and BS lectin. Thus, the membranes of Raji cells incubated in the presence of GSLs contained α-galactosyl epitopes.

Figure 3:
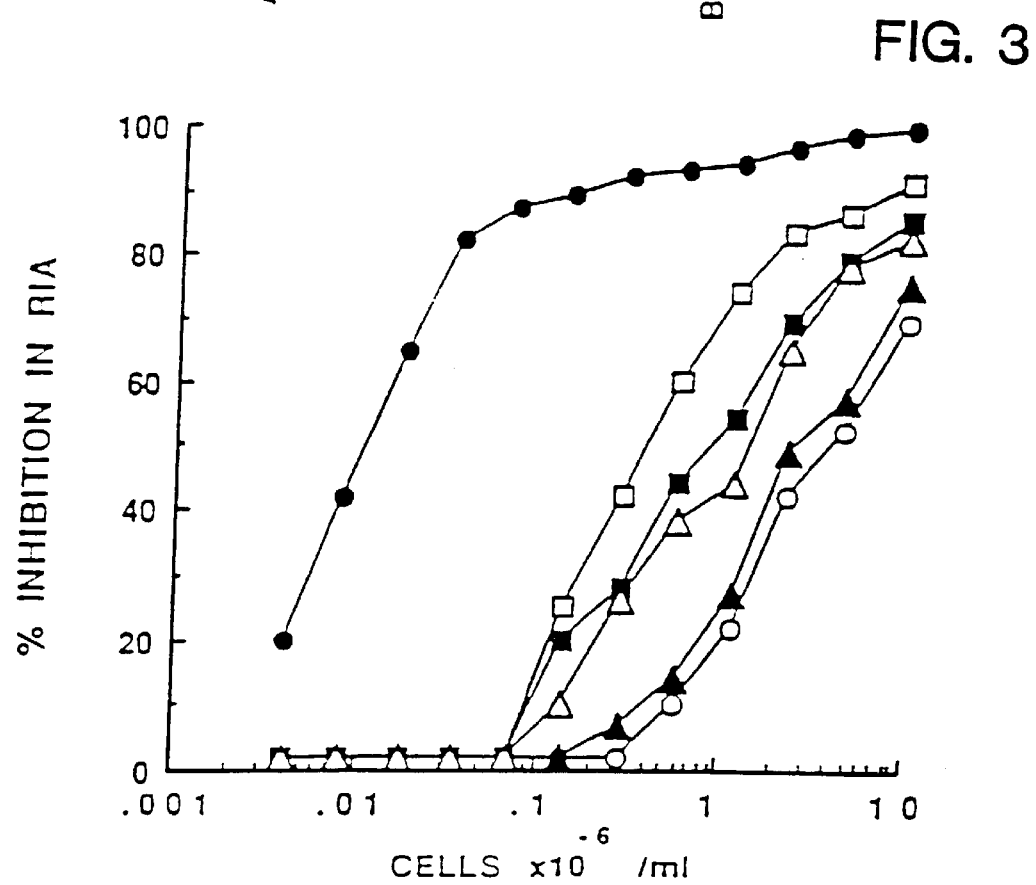
FIG. 3 is a graph depicting measurement of the number of α-galactosyl epitopes bound per cell. The number of α-galactosyl epitopes was assessed in a radioimmunoassay, wherein binding of anti-Gal to test cells was compared with binding of anti-Gal to the marmoset cell line, B95.8 which has been determined by Scatchard plot analysis to express $1.2 \times 10^7$ α-galactosyl epitopes per cell. (●) B98.5 cells; (□) HTB70 cells; (Δ) Raji cells; (▲) ALL-1 cells; (○) Molt4 cells. In addition, HTB70 cells treated with GSL as above followed by incubation at 37° C. for 4 hours in the absence of GSLs prior to fixation were also examined (■).

The number of α-galactosyl epitopes added to cells in the experiment described above was estimated by radioimmunoassay (Thall et al., 1990, Biochemistry 29:3959) (FIG. 3), wherein the marmoset cell line, B958, which contains approximately 1.2×10$^7$ α-galactosyl epitopes per cell, served as a positive control (Galili et al., 1988, J. Biol. Chem. 263:17755). The assay is a competition assay designed to measure the extent of inhibition of binding of biotinylated anti-Gal to immobilized α-galactosyl epitopes in test wells, by α-galactosyl epitopes in suspension. Whereas, control Raji cells did not inhibit binding of anti-Gal even at a concentration of $4 \times 10^6$ cells/ml, Raji cells incubated in the presence of GSLs inhibited binding of anti-Gal by up to 50% at a concentration of $1 \times 10^6$ cells per ml (i.e. 100-fold higher concentration than that required for 50% inhibition of binding by B958 cells). Based upon these results, the number of α-galactosyl epitopes per Raji cell was estimated to be $1.2 \times 10^5$. Three other cell lines were tested for their ability to incorporate α-galactosyl epitopes into their membranes. The human melanoma cell line, HTB70, was observed to incorporate approximately $4 \times 10^5$ epitopes/cell; the pre-B leukemia cell line, ALL-1, incorporated $6 \times 10^4$ epitopes per cell; and, the T leukemia cell line, Molt-4, incorporated approximately $3 \times 10^4$ epitopes per cell.

Figure 4A:
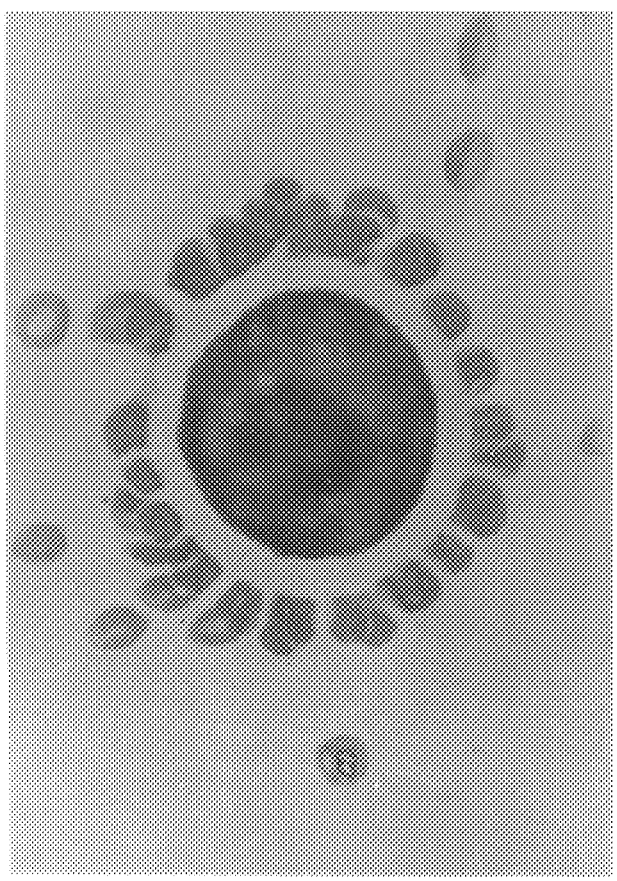
FIG. 4. A. A photomicrograph depicting the interaction of anti-Gal coated red blood cells with human Fc receptors. A mixture of anti-Gal coated red blood cells and the human myeloid cell line K562, was incubated for 30 minutes at room temperature. The micrograph depicts rosette formation resulting from the interaction of the Fc portion of the anti-Gal IgG with Fc receptors on the cells. B. A photomicrograph depicting anti-Gal mediated phagocytosis of rabbit red blood cells by mouse macrophages. Anti-Gal coated rabbit red blood cells were incubated with immobilized mouse macrophages for 2 hours at 37° C. after which the macrophages were washed, fixed and stained with Giemsa. It is evident that the macrophages contain several red blood cells per macrophage, whereas, fibroblasts within the macrophage cell culture (arrowhead) are devoid of red blood cells.
Figure 4B:

The assay described above also enabled an examination of the stability of α-galactosyl epitopes when incorporated into cell membranes. HTB70 cells containing rabbit GSLs were washed and incubated in the absence of GSLs for 4 hours at 37° C., following which they were fixed and assayed for the presence of α-galactosyl epitopes as described above. The data are presented in FIG. 3. Cells so treated contained $2 \times 10^5$ α-galactosyl epitopes per cell, i.e., one half of the number of epitopes present prior to the 4 hour incubation period. When cells were incubated for 20 hours in the absence of GSLs following their addition to cells, a complete loss of α-galactosyl epitope expression was observed. However, the rate at which irradiated cells lose these epitopes is expected to be considerably lower because the turnover rate of membranes in irradiated cells is markedly reduced compared with live cells. Opsonization effected by binding of anti-Gal to α-galactosyl epitopes added to cell membranes as described above was examined as follows. Binding of rabbit red blood cells, which as noted above contain an abundance of α-galactosyl epitopes, to cells of myeloid lineage was assessed in the presence or absence of anti-Gal. It is evident from FIG. 4 that binding of rabbit red blood cells to the human myeloid cell line K562 occurred in the presence of anti-Gal. No binding was observed in the absence of this anti-body. Furthermore, anti-Gal-coated rabbit red blood cells incubated in the presence of mouse macrophages were phagocytosed at a rate which was directly related to the concentration of anti-Gal applied to the cells (FIG. 4). In contrast, negligible phagocytosis of untreated cells was observed (FIG. 4). Therefore, binding of anti-Gal antibody to α-galactosyl epitope containing cells serves to accelerate the rate at which they are phagocytosed.

Figures 5, 7:
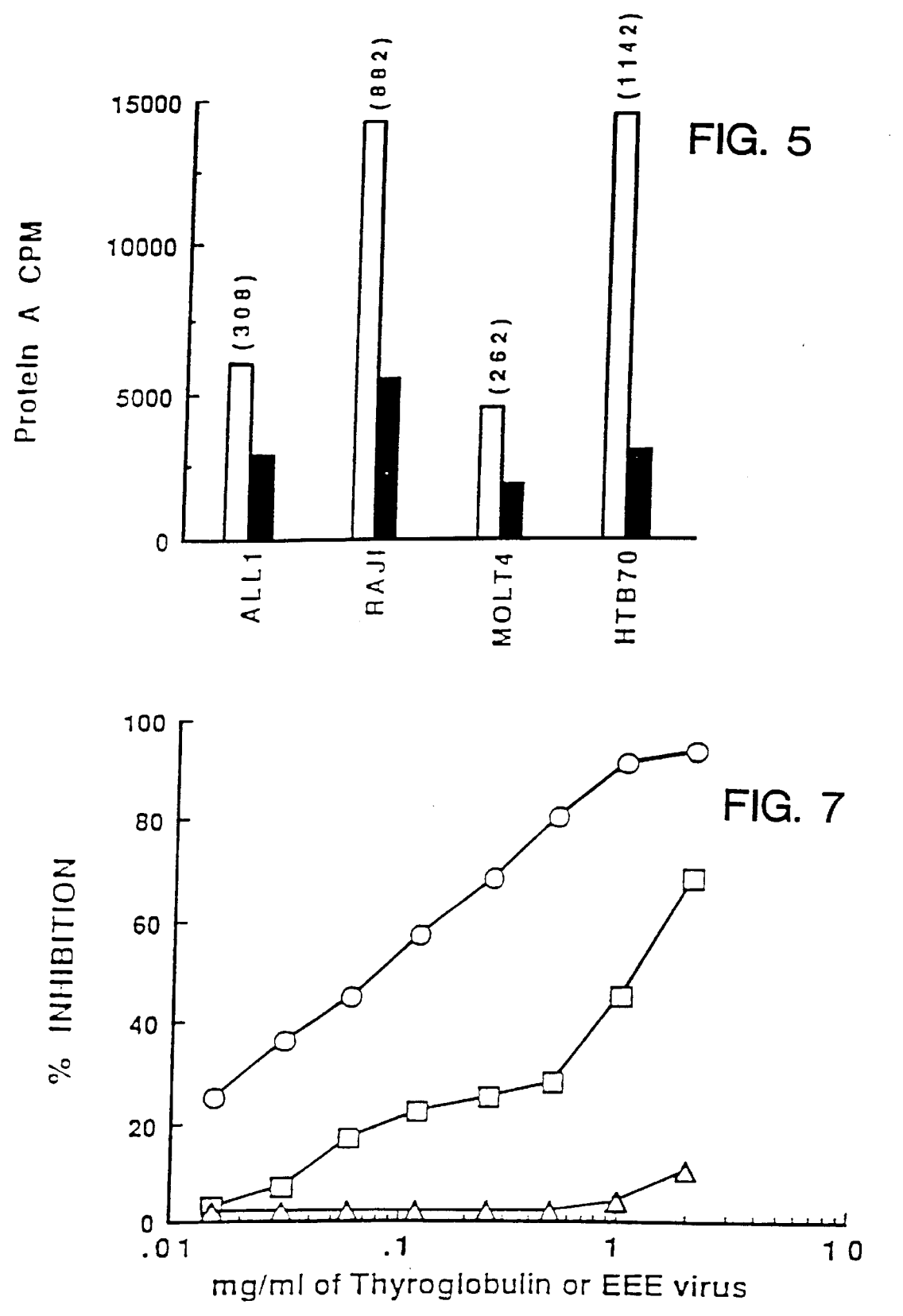

To quantitate the number of anti-Gal IgG molecules bound per cell, cells containing epitopes were incubated with anti-Gal in the presence of $^{125}$I protein A. Since protein A and IgG interact with each other at a ratio of 1:1, the number of anti-Gal molecules per cell can be determined based upon the specific activity of $^{125}$I protein A. As is seen in FIG. 5, binding of $^{125}$I protein A (and therefore anti-Gal) to the four GSL treated cell lines was two- to seven-fold higher than binding of the antibody to untreated cells. In this experiment, approximately 1000 cpm of $^{125}$I protein represented 108 molecules. Thus, the number of anti-Gal molecules bound was calculated to be 262 to 1142 per cell. It is expected that binding of anti-Gal to α-galactosyl epitopes in vivo will be much higher than that observed in vitro because of the stringent washing involved in the in vitro assay which obviously would not be the case in vivo.

These data provide evidence that freshly separated tumor cells may be converted into cells which contain α-galactosyl epitopes on their surface. In addition, the potential for anti-Gal to opsonize tumor cells or membrane fractions thereof is evident from these experiments. Thus, tumor cells obtained from a patient may be treated according to the methods described above. When cells so treated are irradiated and re-administered to the patient from which they were obtained, they will bind anti-Gal thereby enhancing their phagocytosis and subsequent expression of autologous TAAs on the macrophage surface. TAAs so expressed serve to elicit an immune response against all like TAAs including those resident on cells remaining in the tumor, thereby eliciting an immune response against the tumor itself.

The invention is not limited to insertion of α-galactosyl epitopes into membranes of whole cells. Rather, TAA containing cell membranes may be prepared from cells which membranes are then incubated in the presence of GSLs by generally following the methods described above. Alternatively, synthetic membranes may also be useful in the invention. Variations of the methods described above may be required to effect insertion of α-galactosyl epitopes into such membrane preparations. For example, it may be necessary to vary the concentration of the components of the reaction and/or the length of the incubation period, etc., depending upon the type of membrane being used. The invention should be construed to encompass such variations as they will be readily apparent to those skilled in the art given the teaching in the specific examples described above. Successful insertion of α-galactosyl epitopes into membranes can be assessed in binding studies using anti-Gal. Furthermore, opsonization of antigens juxtaposed to such epitopes is assessed by measuring their rate of phagocytosis by macrophages following the methods described above.

Additional membrane preparations may be obtained as follows. Cells are homogenized and the resulting lysate is clarified by centrifugation. Membrane preparations contained within the supernatant are pelleted, resuspended and incubated in the presence of GSLs as described above to effect insertion of GSLs therein. Successful insertion is assessed in the methods described above.

Naturally occurring or synthetic membrane preparations which encapsulate an antigen to be opsonized may be prepared as follows. A preparation of phospholipid such as phosphatidyl choline is mixed with GSLs at a molar ratio of approximately 40:1. A solution comprising the antigen to be encapsulated is added and the mixture is sonicated effecting formation of liposomes containing α-galactosyl epitopes inserted therein which liposomes encapsulate antigen (Galili et al., 1985, J. Exp. Med. 162:573). Similarly, antigens may be directly encapsulated in membranes which naturally contain α-galactosyl epitopes, for example, resealed cell mem- brane ghosts.

Many viral vaccines do not elicit an effective protective immune response in all individuals receiving the vaccine in that age, immunocompetence, etc., all play a role in the quality and magnitude of the response to a given vaccine. Enhancement of an individual's response to a vaccine can be accomplished by opsonization of that vaccine in a manner similar to that described above for tumor cells. Essentially, viruses or subunits thereof comprising the vaccine, are manipulated such that α-galactosyl epitopes are presented on or juxtaposed to the antigens contained within them, which epitopes are then recognized by circulating anti-Gal antibodies upon administration of the vaccine to a patient. Vaccines so opsonized will be more efficiently internalized by macrophages and consequently will be more efficiently processed and presented to T helper cells in association with class II MHC molecules thereby eliciting a more effective immune response. Since anti-Gal IgA antibodies are also secreted in the respiratory and the gastrointestinal tracks, they may also be exploited to interfere with virus infection via these common portals of entry.

Opsonization of viral antigens—Equine encephalitis virus. Expression of α-galactosyl epitopes on viral glycoproteins was assayed using eastern equine encephalitis (EEE) virus, a member of the Togavirus family (Alphavirus genus), as a prototype. The envelope of EEE virus comprises two virus-encoded proteins, E1 and E2, which by sequence analysis have been predicted to possess one and two potential N-linked glycosylation sites, respectively (Chang and Trent, 1987, J. Gen. Virol. 68:2129).

To determine whether α-galactosyl epitopes can be incorporated into the EEE virus envelope, the virus was grown either in mouse 3T3 fibroblasts ($EEE_{3T3}$), which fibroblasts express an abundance of α-galactosyl epitopes (Santer et al., 1989, Eur. J. Biochem. 181:249), or in cells derived from an Old World monkey, Vero cells ($EEE_{vero}$) which lack α1,3GT and α-galactosyl epitopes (Galili et al., J. Biol. Chem. 263:17755 Joziasse et al., 1989, J. Biol. Chem 264:14290). The presence or absence of α-galactosyl epitopes on E1 and E2 was assessed in a western blot assay using anti-Gal antibody and the lectin Bandeiraea simplicifolia IB4 (BS lectin) which, like anti-Gal, interacts specifically with α-galactosyl epitopes (Wood et al., 1979, Arch. Biochem. Biophys. 198:1). The number of α-galactosyl epitopes per virus was calculated using the radioimmunoassay described above, and the effect of anti-Gal on the infectivity of EEE virus was evaluated in a plaque reduction neutralization assay.

Addition of α-galactosyl epitopes to EEE virus. EEE virus, strain 215-85 was obtained from the Yale Arbovirus Research Unit, New Haven, Conn. This virus was originally isolated from a pool of Cs. melanuria mosquitoes and was passaged twice in Vero cells to obtain a stock preparation. Vero or mouse 3T3 fibro-blasts were inoculated with virus at a multiplicity of 0.05–0.1 plaque forming units (PFU) per cell. Cells were incubated in the presence of Eagle minimal essential media (EMEM) supplemented with 5% heat-inactivated fetal bovine serum (FBS), 0.1 mM non-essential amino acids, 1× anti-PPLO agent (all from Gibco), penicillin (100 U/ml) and streptomycin (100 µg/ml). Following incubation at 36° C. for 24 hours cell culture fluids were harvested and centrifuged at 4000×g for 20 minutes to remove cell debris, and the virus was precipitated by the addition of polyethylene glycol 8000 (Sigma Chemical Co., St. Louis, Mo., 70 g/l) and NaCl (23 g/l) at 4° C. for 14 hours. Precipitated virus was collected by centrifugation at 6000×g for 30 min, the pellet was resuspended in a low salt buffer (LSB: 0.15M NaCl, 0.01M Tris-HCl, pH 7.4), and virus was further purified by rate zonal centrifugation through a 20–70% (w/v) sucrose gradient in LSB at 208, 000×g for 90 minutes at 4° C. (Beckman SW 41 rotor). A band of virus formed in the tube which was collected, diluted 4-fold in LSB, and pelleted at 208,000 g for 2 hours at 4° C. through a 1 ml cushion of 20% (w/v) sucrose in LSB.

The resulting virus pellet was resuspended in TE buffer (20 mM Tris-HCl, pH 7.4, 2.0 mM EDTA) and stored at −800° C.

The presence of α-galactosyl epitopes on EEE virus envelope glycoproteins was assessed by immunostaining with purified anti-Gal (Thall et al., 1990, Biochemistry 29:3959) and with BS lectin (Vector Laboratories, Burlingame, Calif.). Proteins derived from 50 µg of EEE virus propagated either in Vero cells or in 3T3 cells were separated by discontinuous sodium dodecyl sulfate polyacrylamide gel electrophoresis (SDS-PAGE) on mini-gels (Mini-PROTEAN II gel system, BioRad, Richmond, Calif.) at 200 V for 30 minutes (Schmaljohn et al., 1983, J. Infect. Dis. 148:1005). Resolved proteins were transferred to a nitrocellulose support, blocked with 10% horse serum, and incubated with purified anti-Gal (10 µg/ml) or horseradish peroxidase (HRP)-conjugated BS lectin (20 µg/ml) for 2 hours at 24° C. Unreacted components were removed by washing and anti-Gal-reactive proteins were visualized by staining with HRP-conjugated rabbit anti-human IgG (secondary antibody) and the substrate 3,3'-diaminobenzidine tetrahydrochloride (DAB) (Sigma). Detection of HRP-BS lectin-reactive proteins was performed by direct addition of the DAB substrate.

Figure 6:
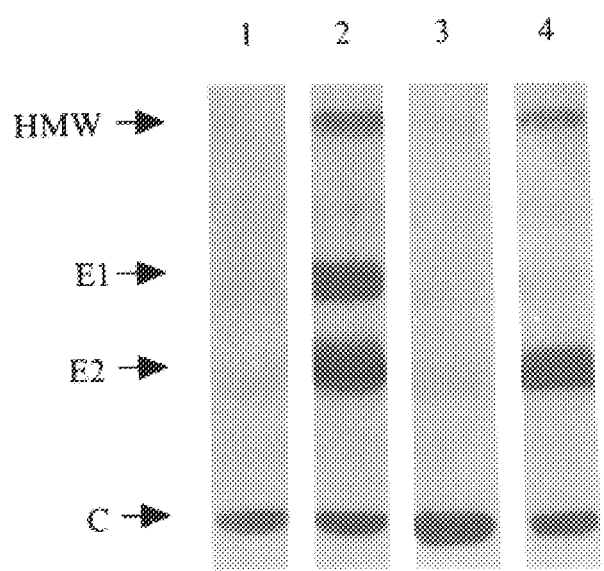
FIG. 6 is a gel depicting immunoreactivity of $EEE_{vero}$ and $EEE_{3T3}$ (eastern equine encephalitis virus propagated in Vero or 3T3 cells, respectively) virion structural proteins with anti-Gal antibody and BS lectin. Lane 1—$EEE_{vero}$ and Lane 2—$EEE_{3T3}$ both reacted with anti-Gal. Lane 3—$EEE_{vero}$ and Lane 4—$EEE_{3T3}$ both reacted with BS lectin. Binding to the capsid protein (C) represents nonspecific binding in all four situation

The results of these experiments are as follows. In FIG. 6 it is evident that $EEE_{3T3}$—specific E1 and E2 glycoproteins contained α-galactosyl epitopes (lane 2). In addition, interaction between anti-Gal and a high molecular weight (HMW) protein composed primarily of E2 molecules, was observed. In contrast, no interaction was observed between anti-Gal and $EEE_{vero}$—specific E1 and E2 glycoproteins or the corresponding HMW protein (lane 1), indicating the absence of α-galactosyl epitopes on these proteins. Immunostaining with BS lectin revealed lectin binding to the E2 and HMW proteins of $EEE_{3T3}$ virus (lane 4) but not to glycoproteins of the $EEE_{vero}$ virus (lane 3). Binding of both anti-Gal and BS lectin to the capsid protein of EEE virus propagated in either cell type was nonspecific in that it could not be eliminated using a blocking solution.

The number of α-galactosyl epitopes per EEE virus particle was assessed in the radioimmunoassay described above. Immobilized α-galactosyl epitope comprised bovine thyroglobulin. Microtiter wells were precoated with thyroglobulin (50 µg/ml) in carbonate buffer (pH 9.5). Aliquots of biotinylated anti-Gal (1 µg/ml) mixed with various concentrations of EEE virus were incubated for 20 hours at 4° C. This mixture was added to the precoated wells and incubation was continued for 1 hour at 24° C. Under these conditions, glycoproteins in solution, or particles in suspension, which lack α-galactosyl epitope do not inhibit binding of anti-Gal to immobilized α-galactosyl epitope whereas glycoproteins which contain the epitope bind to anti-Gal thereby preventing binding of the antibody to the immobilized epitope. The extent of binding of anti-Gal to immobilized epitope was assessed as follows. Reaction mixtures were removed from the wells, the wells were washed with PBS containing 0.05% Tween followed by the addition of 50 µl of $^{125}$I-streptavidin ($10^5$ cpm). The mixture was incubated for an additional 1 hour at 24° C. after which the wells were again washed to remove unbound avidin. Next, 100 µl of 0.2N HCl was added to the wells in order to detach $^{125}$I streptavidin bound to anti-Gal. A standard curve was generated using bovine thyroglobulin since it is known that each molecule contains an average of eleven α-galactosyl epitopes (Spiro et al., 1984, J. Biol. Chem. 259:9858). Thus, the amount of radioactivity contained within each 100 µl test sample when determined served as a measure of the number of α-galactosyl epitopes per virion. The results of this experiment are presented in FIG. 7.

An inhibition of binding by $EEE_{Vero}$ of 15% at a viral concentration of 2 mg/ml represents nonspecific inhibition likely due to the high concentration of virus particles in the assay, since as noted above, $EEE_{Vero}$ does not contain α-galactosyl epitopes. $EEE_{3T3}$ exhibited 50% inhibition in the assay at a viral concentration of 1 mg/ml and 20% inhibition at a concentration of 0.06 mg/ml. Control bovine thyroglobulin at a concentration of 0.07 mg/ml (corresponding to 100 nmole/ml) exhibited a 50% inhibition in the assay. These data indicate that the $EEE_{3T3}$ virus contained approximately 80 α-galactosyl epitopes per virus particle according to the following calculation: 50% inhibition by bovine thyroglobulin represents a neutralizing effect of $6.6 \times 10^{14}$ α-galactosyl epitopes present on 100 nmole of thyroglobulin (1 nmole thyroglobulin=$6 \times 10^{11}$ molecules and each molecule contains 11 α-galactosyl epitopes). An inhibition of 50% was observed in the case of $EEE_{3T3}$, therefore the same number of epitopes were present in 1 mg/ml of $EEE_{3T3}$ virus particles as in 0.07 mg/ml of thryoglobulin. The average molecular weight of each of E1 and E2 is approximately 50,000 (E1: 53,000; E2: 42,000–43, 500) and it is estimated that these glycoproteins comprise 50% of the weight of the virus (Koblet, 1990, Adv. Virus Res. 38:343). Thus, 50% inhibition by $EEE_{3T3}$ corresponds to 0.5 mg of $EEE_{3T3}$ glycoproteins, which in turn corresponds to 10 nmole, or approximately $4 \times 10^{15}$ glycoprotein molecules. This number of molecules contained a total of $6.6 \times 10^{14}$ α-galactosyl epitopes indicating that one out of six $EEE_{3T3}$ glycoprotein molecules contain an α-galactosyl epitope bound thereon. Since each EEE virion is estimated to contain approximately 480 E1 and E2 molecules (Fuller, 1987, Cell 48:923), the number of α-galactosyl epitopes was calculated to be approximately 80 per $EEE_{3T3}$ virus particle.

A plaque reduction neutralization test (PRNT) was used to assess the neutralizing activity of anti-Gal on purified preparations of EEE virus propagated in 3T3 and in Vero cells. Serial two-fold dilutions of anti-Gal antibody, ranging from 1:2.5 to 1:80 (representing 40 μg/ml to 1.25 μg/ml antibody, respectively), were prepared in serum-free EMEM. An aliquot of each dilution was added to an equal volume of virus (at a concentration of 100–150 PFU/0.1 ml), and the virus-antibody mixtures (0.5 ml total volume) were incubated at 37° C. for 30 min, followed by 18 hours at 4° C. The amount of infectious virus remaining in the mixture was measured by plaque assay on Vero cell monolayers in the presence of anti-Gal antibody at a concentration of 2.5 to 40 μg/ml. Plaque assays were performed following standard protocols.

Figure 8A:
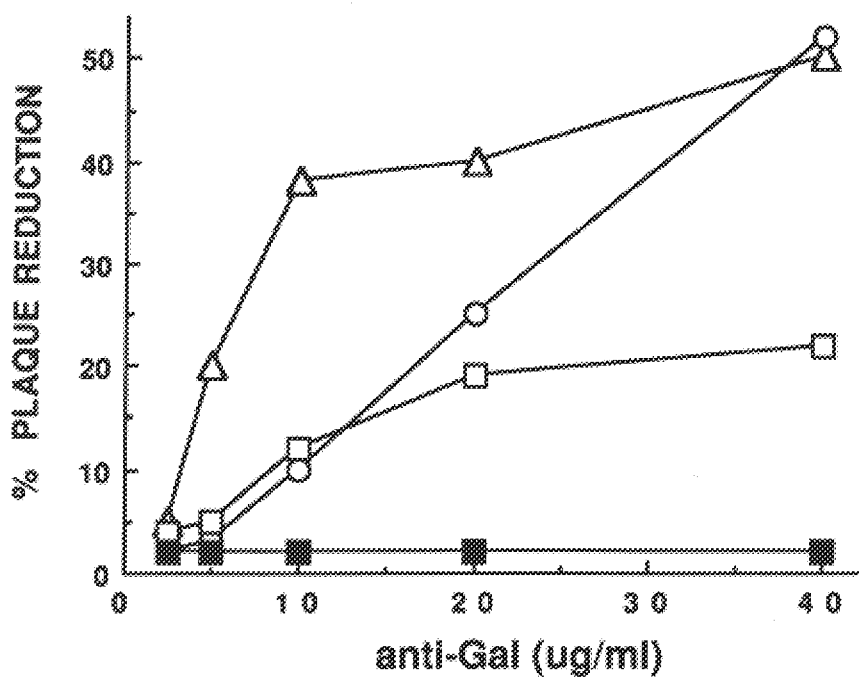
FIG. 8. A. A graphical representation of plaque reduction neutralization of $EEE_{Vero}$ and $EEE_{3T3}$ viruses induced by anti-Gal. The percent of plaque reduction versus amount of anti-Gal is shown for $EEE_{Vero}$ (■), and $EEE_{3T3}$ (○, □, Δ), each symbol representing a separate experiment with this virus. B. A photograph of a representative plaque reduction neutralization assay using $EEE_{3T3}$ and 0, 20, 10, 5, 2.5, and 1.25 μg/ml anti-Gal as indicated.
Figure 8B:
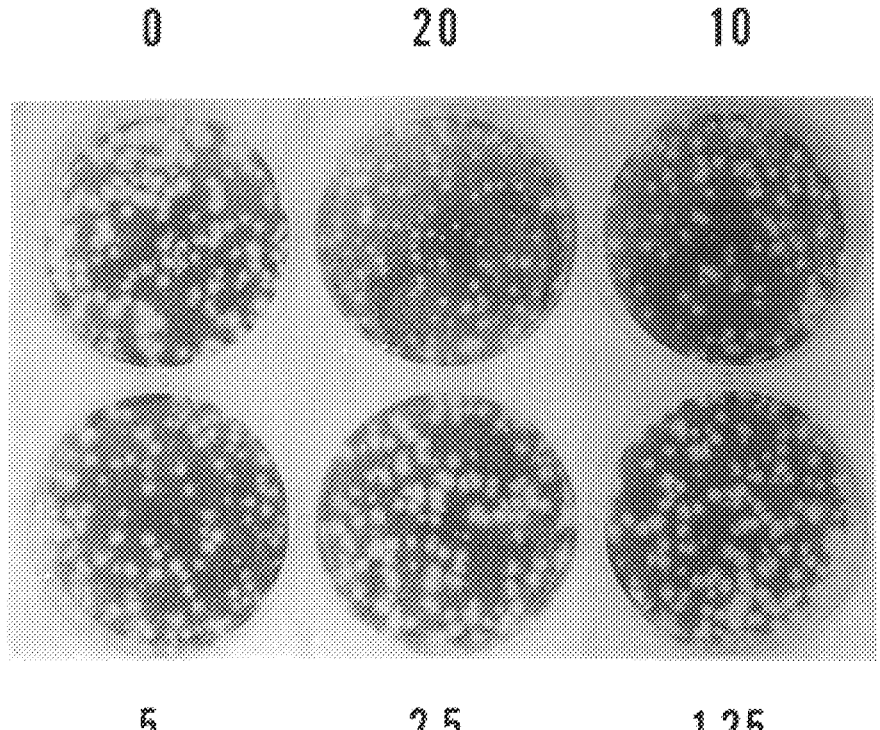

In three separate experiments, anti-Gal had no effect on plaque formation by $EEE_{vero}$. In contrast, incubation of $EEE_{3T3}$ with as little as 40 μg/ml anti-Gal resulted in a 20–50% decrease in plaque formation (FIG. 8A). In addition, plaques so formed were significantly smaller (0.5 to 1 mm average diameter) than those in control non-antibody treated cultures (2 mm average diameter) (FIG. 8B). The relative size of the plaques increased with decreased antibody concentration. Neutralization of $EEE_{3T3}$ was evident at anti-Gal concentrations as low as 10 μg/ml (FIG. 8B).

Opsonization of Viral Antigen—Influenza Virus. The following study demonstrates the presence of α-galactose epitopes on influenza virus, and the ability of anti-Gal to enhance viral antigen processing and presentation when virions express α-galactosyl epitopes.

Introduction. Since the hemagglutinin molecule of influenza virus has several glycosylation sites in the external region of the molecule (Winter et al., 1982, Nature 290:72; Ward et al., 1980, Virology 103:37), which sites comprise complex carbohydrate chains containing n-acetyllactosamine, it is expected that some of these sites will be "capped" with terminal α-galactosyl to form α-galactosyl epitopes in Madin Darby Bovine Kidney (MDBK) cells or Madin Darby Canine Kidney (MDCK) cells, since born contain α1,3GT. Influenza virus is propagated in a manner similar to that described above for EEE virus, except that trypsin at a concentration of approximately 1 μg/ml is added to the culture medium (Parvin et al., 1986, J. Virol. 59:377; Brand et al., 1980, Virology 107:424).

Anti-Gal was used to enhance the in vitro antigen processing and presentation of the hemagglutinin (HA) molecule of the $H_1N_1$ inactivated influenza virus A/Puerto Rico/8/34 (termed PR8 virus), when virions express α-galactosyl epitopes. The HA molelcule of the invluenza virus has seven asparagine (N)-linked carbohydrate chains (Kiel et al., 1985, Embo J. 4:2711), which can serve as core structures for the synthesis of α-galactosyl epitopes. Virions expressing this carbohydrate epitope were obtained by propagation of the virus in bovine and canine cells which have α1,3GT. PR8 virus propagated in embryonated eggs lacks α-galactosyl epitopes since fowl do not have α1,3GT (Galili et al., 1988, J. Biol. Chem. 263:17755). The extent of antigen processing in BALB/c mouse spleen APC was assessed by measuring the stimulation for proliferation of syngeneic monoclonal $T_H$ cells specific for peptide epitopes on the HA molecule (Gerhard et al., 1983, J. Immunol. 130:2379; Gerhard et al., 1991, J. Virol. 65:364).

Virus Preparation and Inactivation. Influenza virus strain A/PR/8/34($H_1N_1$) (PR8 virus) was propagated in the allantoic cavity of 11-day-old embryonated eggs (termed $PR8_{egg}$ virus), or on monolayers of Madin Darby Bovine Kidney (MDBK) cells ($PR8_{MDBK}$ virus), or Madin Darby Canine Kidney (MDCK) cells ($PR8_{MDCK}$ virus). Following inoculation of cell monolayers, virus was grown at 360° C. in serum-free Dulbecco's MEM (Mediatech, Washington, D.C.) supplemented with 1 μg of TPCK trypsin (Sigma) per ml (Parvin et al., 1986, J. Virol., 59:377). The virus was precipitated from allantoic fluids and cell supernatants by polyethyleneglycol and purified on a continuous sucrose gradient as previously described (Strizki et al., 1994, J. Gen. Virol. 75:2897). Protein concentration was measured by color reaction using the Pierce BCA Protein Assay (Pierce, Rockford, Ill.). Virus titer in each preparation was measured by both hemagglutination assay (with chicken red cells), and expressed as HA units (HAU) per ml, and by plaque assay as previously described (Repik et al., 1983, Am. J. Trop. Med. Hyg. 32:577) on MDCK cell monolayers, overlaid with serum-free Dulbecco's MEM containing 0.4% agarose and 1 μg/ml TPCK trypsin.

Demonstration of α-galactosylGalactosyl Epitopes on PR8 Virus. The presence of α-galactosyl epitopes on virus was determined with BS lectin, which interacts specifically with α-galactosyl epitopes (Wood et al., 1979, Arch. Biochem. Biophys. 198:1), and with anti-Gal, in ELISA and in western blots. For ELISA, purified virus in carbonate buffer pH 9.5 was dried in 96-well plates (1 μg virus per well). After blocking with 1% BSA in PBS, biotinylated BS lectin or biotinylated anti-Gal were added to each well in serial two-fold dilutions, starting at concentrations of 20 μg/ml and 2.5 μg/ml respectively. After 1 hour incubation at room temperature, the plates were washed with PBS containing 0.05% Tween 20, incubated for 1 hour with 0.1 ml avidin-HRP diluted 1:1000, washed, and color produced by incubation with 0.1 ml of 1 mg/ml O-phenylenediamine in phosphate buffer, pH 5. The reaction was stopped after 30 minutes with 50 μl of 0.1M sulfuric acid, and absorbance was measured at 492 nm in a TITERTECK ELISA plate reader.

Figure 12B:
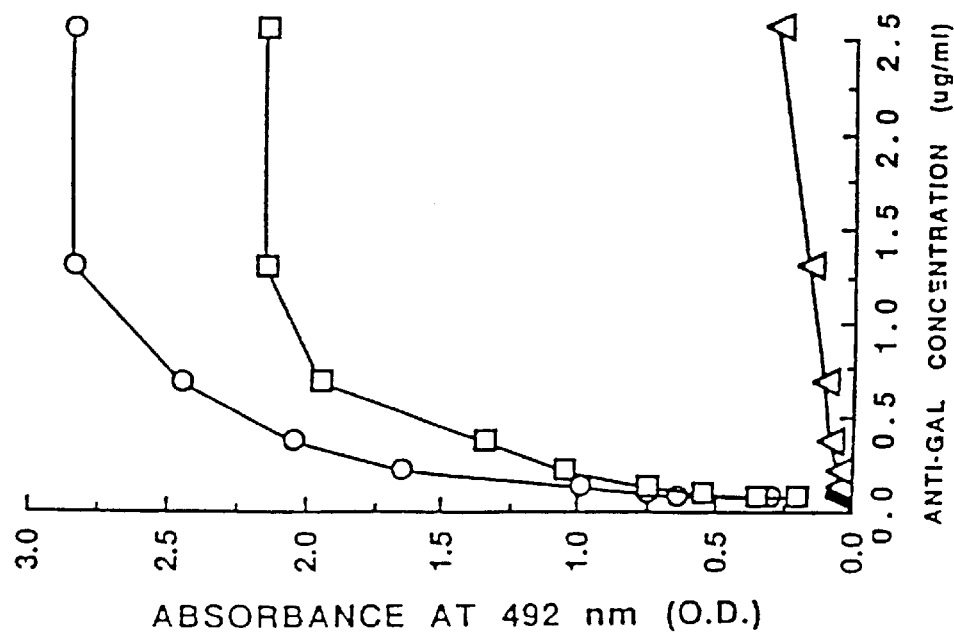
FIGS. 12A and 12B are plots of BS lectin (12A) and anti-Gal antibody (12B) binding to PR8 virus propagated in various cells. ○, $PR8_{MDBK}$ virus; □, $PR8_{MDCK}$ virus; Δ, $PR8_{egg}$ virus. The binding was determined in ELISA using different concentrations of biotinylated lectin or antibody, then avidin-HRP. Data is shown from one experiment of three such experiments with similar results.
Figure 12A:
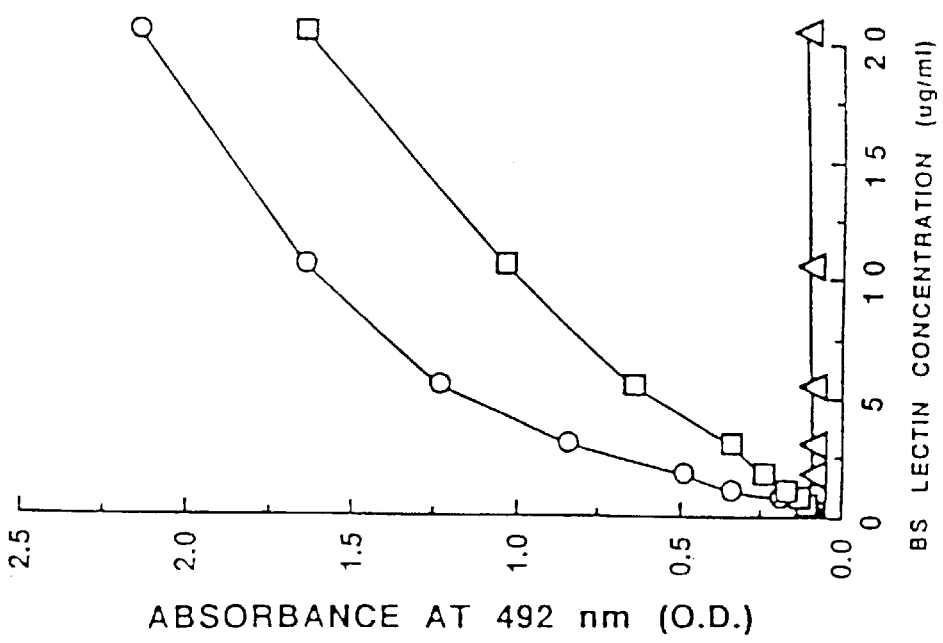

As shown in FIG. 12A, no lectin binding was observed with the $PR8_{egg}$ virus; however, BS lectin readily bound to the $PR8_{MDCK}$ virus and to a higher extent to the $PR8_{MDBK}$ virus. This is in accord with previous findings that canine and bovine cells synthesize α-galactosyl epitopes whereas chicken, as other fowl, lack this epitope (Galili et al., 1988, J. Biol. Chem. 263:17755). Similarly, and as expected, anti-Gal also readily bound to the $PR8_{MDCK}$ virus and to an even greater extent to the $PR8_{MDBK}$ virus (FIG. 12B), but not to $PR8_{egg}$ virus. It should be stressed that for this assay, anti-Gal was first treated with 0.05 U/ml of neuraminidase to remove sialic acid from the antibody's carbohydrate chains. This desialylation step was necessary in order to prevent nonspecific binding of the antibody to the virus via the interaction of the HA with sialic acid residues on the carbohydrate chains present on the Fc part of the antibody molecules.

Western Blot Analysis. The differential binding of anti-Gal to virus propagated in the different cells could be further demonstrated by Western blot analyses. Virus proteins derived from 10 μg of purified virus preparations were separated by SDS-PAGE with a 13% polyacrylamide resolving gel and 3.6% polyacrylamide stacking gel (Mini-PROTEAN II gel system) at 200 V for 20 minutes. Following transfer of the proteins to IMMOBILON-P membranes (Millipore), the blots were blocked overnight with 1% horse serum and immunostained with biotinylated anti-Gal (10 μg/ml), followed by incubation with the VECTASTAIN ABC-HRP reagent (Vector Laboratories, Burlingame, Calif.) and diamino benzidine substrate.

Figure 13:
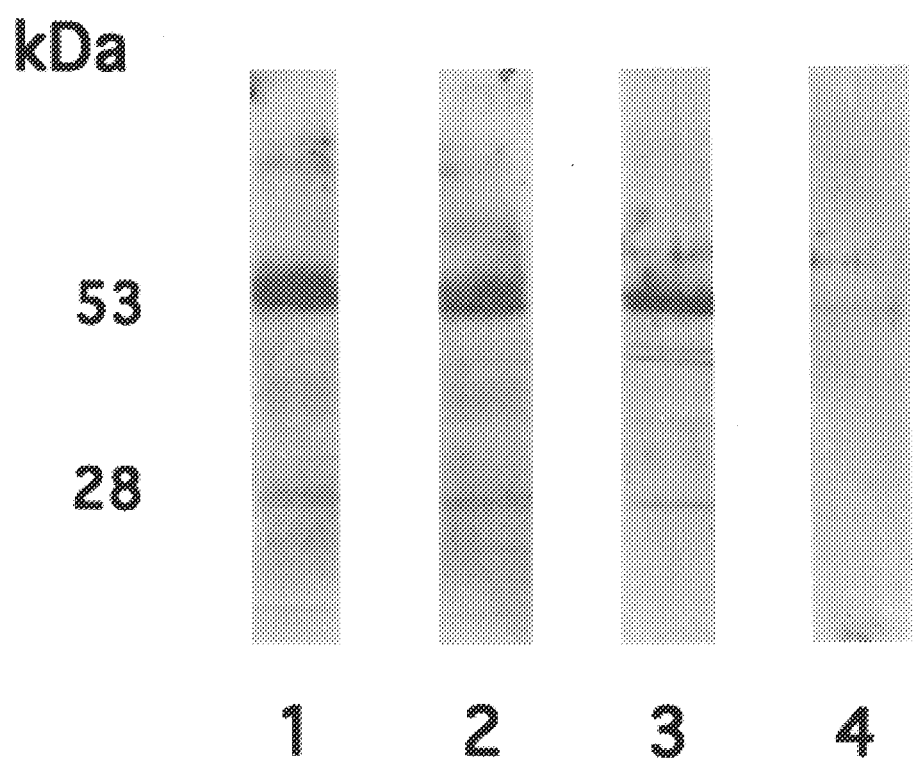
FIG. 13 is a Western blot demonstration of the interaction of anti-Gal with hemagglutinin fragments $HA_1$ (m.w. 53,000) and $HA_2$ (m.w. 28,000) of $PR8_{MDBK}$ virus (lane 1)

As shown in FIG. 13, anti-Gal intensively stained a 53 Kda band of the $PR8_{MDBK}$ virus (lane 1). This band corresponds to the $HA_1$ fragment of the HA molecule, which contains five glycosylation sites (Kiel et al., 1985, Embo J. 4:2711; Air et al., 1990, "Influenza Viruses" in *Immunochemistry of Viruses*, Elsevier Science Publications, eds. M. H. V. van Regemorted and A. P. Neurath, p. 171). Note that the carbohydrate chains of the $PR8_{MDBK}$ virus are larger than those on the $PR8_{egg}$ virus since the former contains four antennae per chain whereas the latter contain two antennae per chain (Kiel et al., 1985, Embo J. 4:2711; Deom et al., 1985, J. Biol. Chem. 260:14771). Therefore, the size of $HA_1$ in $PR8_{MDBK}$ virus is larger by several Kda than that in the $PR8_{egg}$ $HA_1$ (Air et al., 1990; Deom et al., 1985; Schulze I. T., 1970, Virology 41:890). The $HA_2$ fragment (28 Kda), which contains two glycosylation sites (Kiel et al., 1985; Air et al., 1990) is stained to a lesser degree by anti-Gal. Inactivation of the $PR8_{MDBK}$ virus with formalin did not affect the expression and reactivity of the α-galactosyl epitopes (lane 2). Strong immunostaining of $HA_1$ was also observed with the $PR8_{MDCK}$ virus (lane 3), although the staining was somewhat less intense than that observed with the $PR8_{MDBK}$ virus. The lower amount of α-galactosyl epitopes present on $PR8_{MDCK}$ virus, compared to $PR8_{MDBK}$ virus, may possibly be due to a lower activity of the cellular α1,3GT. No significant immunostaining was observed with HA subunits of the $PR8_{egg}$ virus (lane 4), in agreement with the finding that chicken cells lack α1,3GT (Galili et al., 1988, J. Biol. Chem. 263:17755).

HA Antigen Processing Assay. Processing of inactivated PR8 virus HA molecules from virus propagated in embryonated eggs, MDBK, or MDCK cells was determined following incubation of the viruses with anti-Gal and comparison with the processing of HA molelcules from viruses which were not incubated with this antibody. The assay is based on measuring [³H] thymidine incorporation in HA specific $T_H$ clones. The $T_H$ clones have been described in detail (Gerhard et al., 1991, J. Virol. 65:364). Briefly the HA specific $T_H$ clones were generated from BALB/c mice immunized with the PR8 virus. These $T_H$ clones were found to express T cell receptors for defined oligopeptide regions on the influenza virus HA molelcule.

The APC used in the assay were irradiated (2200r) splenocytes from naive BALB/c mice. Each microtiter well contained serial dilutions of 50 μl of formalin inactivated PR8 virus propagated in various cells. All virus preparations (except if specifically stated) were 20 inactivated in formalin and the initial concentration of the virus corresponded to one HAU of the virus preparation before inactivation. The PR8 virus preparations were either incubated with anti-Gal (100 μg/ml) or in PBS prior to the assay. To each well were added 100 μl aliquots of APC ($4 \times 10^6$ irradiated splenocytes/ml) and 50 μl of the various $T_H$ clones ($3 \times 10^5$ lymphocytes/ml) with specific receptors to HA peptides (Gerhard et al., 1991, J. Virol. 65:364). After 48 hours incubation at 37° C. in a 50% $CO_2$ humidified atmosphere, 1 μCi of [³H] thymidine was added to each well. The cells were incubated for additional 16 hours at 37° C., harvested onto filters and [³H] thymidine incorporation measured in a liquid scintillation analyser (Packard). Assays were formed in triplicate and the data are expressed as the mean cpm for each virus dilution. The data with one representative clone of five $T_H$ clones are shown in FIGS. 14A, 14B, 14C.

Preincubation with anti-Gal did not alter the thymidine incorporation in the cultures containing the $PR8_{egg}$ virus as this virus lacks α-galactosyl epitopes (FIG. 14A). In contrast, anti-Gal opsonized $PR8_{MDBK}$ virus was approximately ten-fold more potent in stimulating $T_H$ clones than nonopsonized $PR8_{MDBK}$ virus, i.e., the non-opsonized sample required ten times more viral antigen than the opsonized sample for an equivalent $T_H$ response (FIG. 14B). The proliferation of $T_H$ cells observed with the $PR8_{MDCK}$ virus was lower than that with the $PR8_{DBKK}$ virus or the $PR8_{egg}$ virus (FIG. 14C), probably because of differences in the viral preparations. However, also in this preparation, opsonization with anti-Gal increased by ten-fold the stimulatory potency of the virus preparation. Similar findings were made with four additional $T_H$ clones studied.

Opsonization of antigens other than TAAs, and EEE and influenza antigens. As noted above, the invention is not limited to opsonization of tumor cells, EEE virus and influenza virus. It is evident from the data presented above that the amount of anti-Gal which binds to α-galactosyl epitopes is directly related to the number of α-galactosyl epitopes per antigen. For example, there -is shown above a direct relationship between the amount of anti-Gal bound to EEE and the number of α-galactosyl epitopes present on the virus. There is also shown above a direct relationship between the amount of anti-Gal bound to red blood cells and their phagocytosis by macrophages.

The majority of viruses which have glycoproteins as a component of the virion contain N-acetyl-lactosamine as the terminal structure which is capped with sialic acid (SA) generating the structures: SAα2-3Galβ1-4GlcNAc-R or SAα2-6Galβ1-4GlcNAc-R (Robbins et al., 1977, Cell 12:893; Burke et al., 1976, J. Virol. 20:676). In vitro synthesis of α-galactosyl epitopes on virion envelopes such as these is therefore a two step reaction in which the terminal sialic acid is first removed using neuraminidase (I) followed by covalent attachment of α-galactosyl moieties to the N-acetyllactosamine residues using α1,3GT (II).

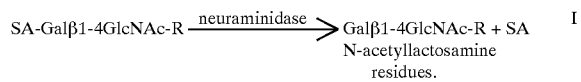

I

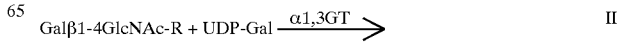

II

Galα1-3Galβ1-4GlcNAc-R + UDP
α-galactosyl epitope.

Since influenza virus lacks sialic acid (Kiel et al., 1985, EMBO J. 4:2711), N-acetyllactosamine residues on this virus are available as receptors for α-galactosyl epitopes without the need for step I above.

Cloning and characterization of marmoset α1,3GT. To obtain a convenient source of the enzyme α1,3GT from primates for catalysis of the addition of α-galactosyl epitopes to carbohydrates, the marmoset gene encoding α1,3GT was cloned and expressed. This enzyme has previously been cloned from both murine and bovine cDNA libraries (Larsen et al., 1989, Proc. Natl. Acad. Sci. USA 86:8227; Joziasse et al., 1989, J. Biol. Chem. 264:14290; Joziasse et al., 1992, J. Biol. Chem. 35 267:5534).

The source of the materials used in the experiments described below are as follows: Radioactive nucleotides were obtained from New England Nuclear (Boston, Mass.). Restriction enzymes, the Klenow fragment of DNA polymerase, T4 DNA ligase and lipofectin were purchased from Bethesda Research Laboratory (Gaithersburg, Md.). IgG agarose, N-acetyllactosamine, lactose and galactose were from Sigma Chemicals (St. Louis, Mo.). Vent™ polymerase for polymerase chain reaction was purchased from Promega (Madison, Wis.).

A marmoset cDNA library was constructed using mRNA extracted from the marmoset (New World monkey) cell line B95.8 (Joziasse et al., 1989, J. Biol. Chem. 264:14290). Poly $A^+$ RNA of $\geq 1$ kb was obtained and the corresponding cDNA was synthesized and ligated into the plasmid pcDNA1 (Invitrogen, San Diego, Calif.) using BstXI linkers. This plasmid, derived from pCDM8, is an expression vector comprising the SV40 origin of replication (Seed et al., 1987, Proc. Natl. Acad. Sci. USA 84:3365). The resulting marmoset cDNA library was screened for the presence of α1,3GT sequences using murine α1,3GT cDNA (Larsen et al., 1989, Proc. Natl. Acad. Sci. USA 86:8227) using screening procedures common in the art (Sambrook et al., 1989, Molecular Cloning: A Laboratory Manual. Cold Spring Harbor, N.Y.). Ten positive clones were characterized by sequence analysis (Sanger et al., 1977, Proc. Natl. Acad. Sci. USA 74:5463) only one of which contained the full length open reading frame encoding the enzyme (FIG. 9).

Figure 10:
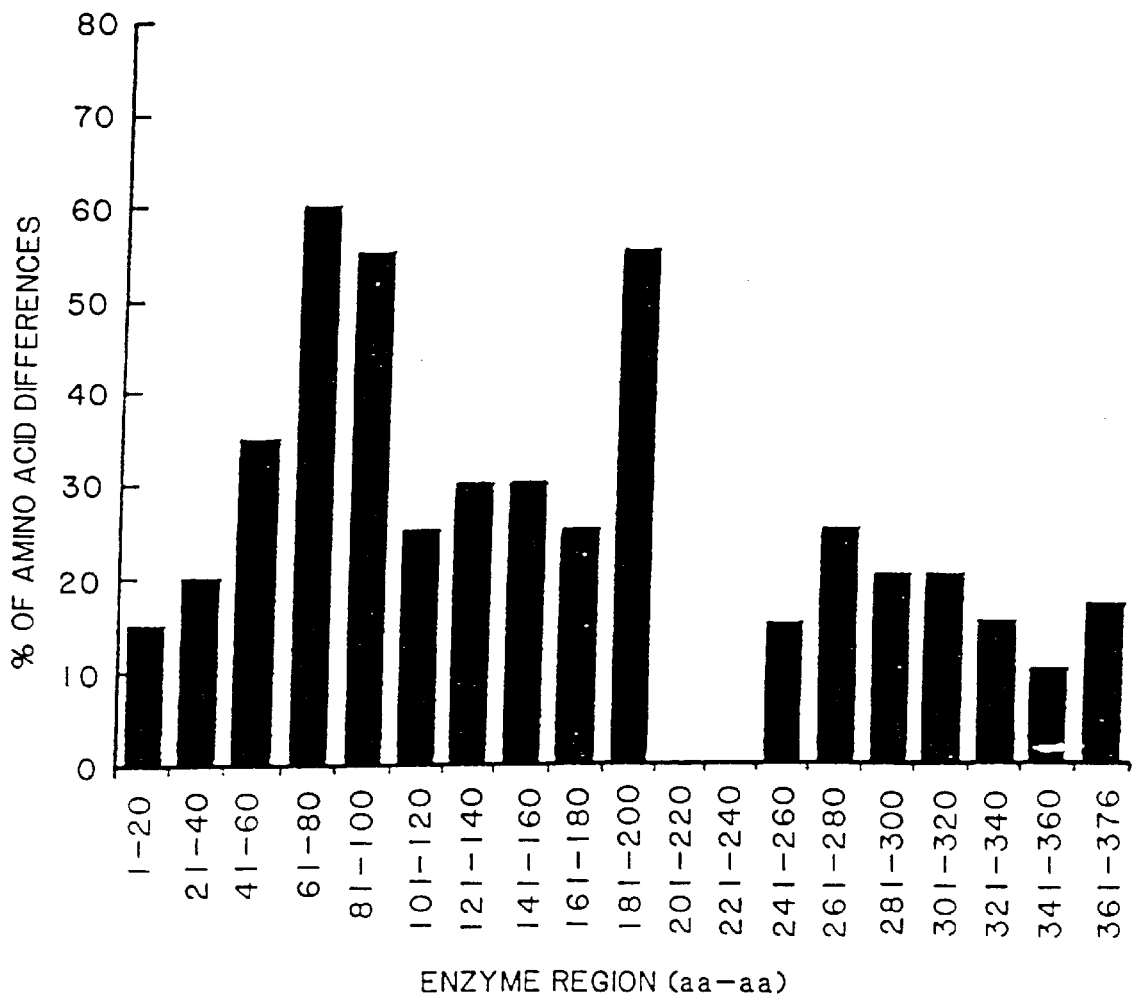
FIG. 10. A comparison of the amino acid composition of marmoset and murine α1,3GT in sections of 20 amino acids. The carboxyl terminus set comprises 16 amino acids.

The predicted characteristics of the cloned marmoset α1,3GT enzyme can be summarized as follows. The enzyme has 376 amino acid residues and is homologous to exons IV through IX of the murine α1,3GT gene (Joziasse et al., 1992, J. Biol. Chem. 267:5534). Consistent with the general topology of glycosyltransferases (Paulson et al., 1989, J. Biol. Chem. 264:17615; Joziasse, 1992, Glycobiology 2:217) there are 6 amino acids in the cytoplasmic domain, 16 amino acids in the transmembrane domain and 354 amino acids in the luminal domain. There is an 18% difference between nucleotide sequence of marmoset and murine α1,3GT (Larsen et al., 1989, Proc. Natl. Acad. Sci. USA 86: 8227; Joziasse, 1992, J. Biol. Chem. 267:5534). Marmoset α1,3GT cDNA also contains 15 bases (corresponding to amino acids 85 to 89) not present in the full length murine sequence. A comparison of the deduced amino acid sequence of murine and marmoset α1,3GT in sections of twenty amino acids each, demonstrates location-dependent variation in amino acid composition (FIG. 10). The regions with the fewest amino acid differences ($\leq 15\%$) are between amino acids 204 and 240, and 321 and 376. Other regions, such as those between amino acids 101 and 200 and between 261 and 320 have amino acid compositions which vary by 20 to 50% and thus may not be required for catalytic activity. The transmembrane region, also displays a high level of similarity to the mouse sequence suggesting conservation of Golgi retention signals (Masilbay et al., 1993, J. Biol. Chem. 268:9908).

COS-1 cells are Old World monkey cells and therefore do not express α1,3GT mRNA (Joziasse et al., 1989, J. Biol. Chem. 264:14290). Because these cells encode the SV40 T-antigen they are suitable hosts for the expression of α1,3GT residing on an SV40-origin containing plasmid. Monolayers of COS-1 cells in 60 mm dishes were transfected with 10 gg of purified plasmid using lipofectin (BRL) and procedures provided by the manufacturer. Cells were incubated in 3 ml serum free Dulbecco Minimal Essential Medium (DMEM) for 18 hours prior to being supplemented with an equal volume of DMEM containing 20% FCS. Incubation was continued for 3 days at 37° C., after which the medium was harvested, clarified by centrifugation and a 10 $\mu$l aliquot of IgG Sepharose beads (Sigma), Tris-HCl (pH 8.0) and Tween-20 (at final concentrations of 5 mM and 0.05%, respectively) were added. The mixture was incubated overnight at 4° C., whereupon the beads with attached enzyme were collected by centrifugation.

The activity of the enzyme was determined essentially as described by Larsen et al. (1989, Proc. Natl. Acad. Sci. USA 86:8227). Five $\mu$l of washed beads equilibrated in 100 mM Tris (pH 8.0) was added in an equal volume of PBS/1% BSA to a reaction mixture containing 50 mM 2-[N-Morpholino] ethanesulfonic acid buffer, pH 6.0, 25 mM $MnCl_2$, 0.2% Triton X-100, 0.2 $\mu$Ci $^3$H-UDP-Gal (New England Nuclear—specific activity 18.9 Ci/mmol), and 10 $\mu$of N-acetyllactosamine in a final volume of 50 $\mu$. The mixture was incubated at 37° C. for 2 hours. Transfer of $^3$H-galactose from $^3$H-UDP-Gal to N-acetyllactosamine was determined following ion exchange chromatography (Larsen et al., 1989, Proc. Natl. Acad. Sci. USA 86:8227).

Figure 11:
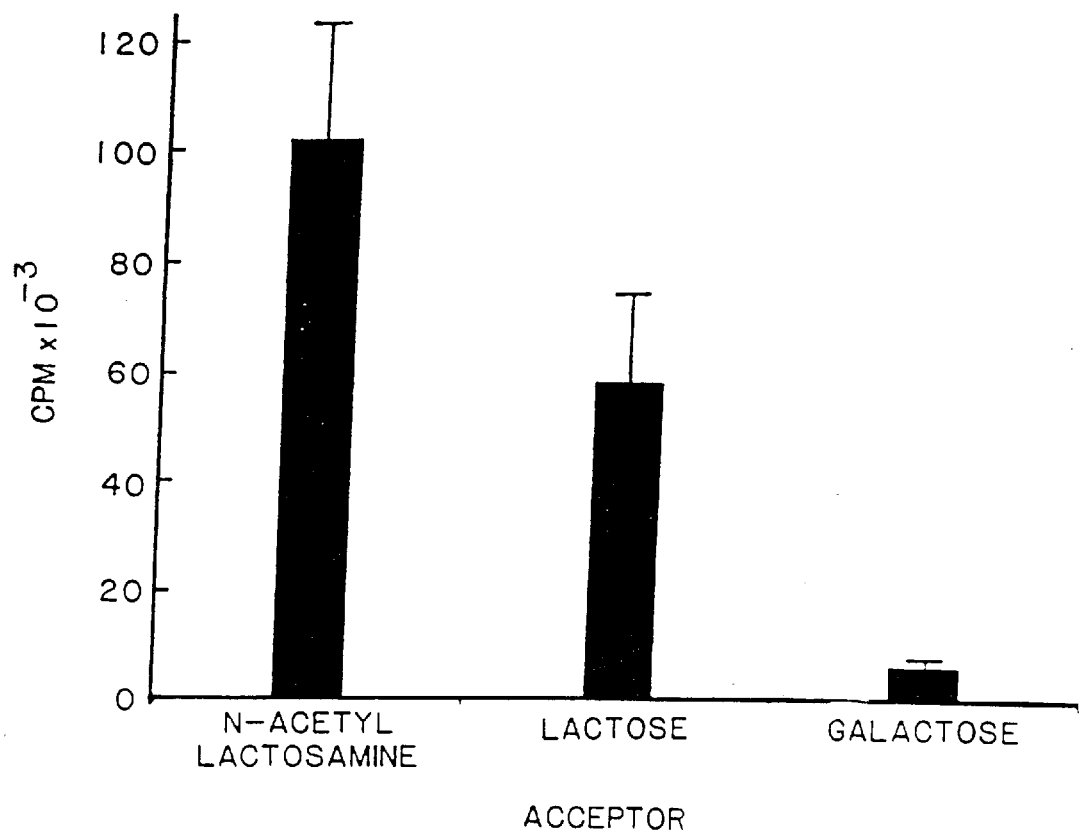
FIG. 11 is a graphical representation of the transfer of $^3$H-Gal to various carbohydrate acceptors by recombinant marmoset α1,3GT secreted by transfected COS cells. The data represent the mean±the standard deviation of the results of five separate transfection studies.

Approximately 40% of the total amount of $^3$H-galactose was transferred to N-acetyllactosamine by the recombinant marmoset enzyme within 2 hours of incubation corresponding to an activity of 0.04 pmole/min. Lactose was 50% less effective than N-acetyllactosamine as an acceptor and galactose was a poor acceptor (FIG. 11). Thus, marmoset α1,3GT displays an acceptor specificity similar to that observed for the murine (Elices et al., 1986, J. Biol. Chem. 261:6064) and bovine (Blanken et al., 1985, J. Biol. Chem. 260:12927) enzymes.

Preparations of recombinant α1,3GT enzyme are obtained from transfected COS cells at approximately three days post-transfection. The supernatant obtained from transfected cells is incubated overnight in the presence of IgG-linked sepharose beads under constant rotation at 4° C. The enzyme is eluted from the beads with glycin-HCl buffer at approximately pH 2.6 which is then immediately neutralized with 0.1N NaOH. Alternatively, the enzyme is obtained from transfected cell supernatants by incubation at 4° C. overnight in the presence of hexanolamine-linked sepharose beads and 5 mM $MnCl_2$. In this case, enzyme is eluted from the beads by addition of 10 mM UDP-Gal which interacts with the enzyme and thus promotes release of the enzyme from the beads (Elices et al., 1986, J. Biol. Chem. 261:6064; Blanken et al., 1985, J. Biol. Chem. 260:12927). UDP-Gal is removed from the mixture by dialysis. The activity of the eluted enzyme is assessed by measuring transfer of $^3$H-Gal from UDP-Gal to N-acetyllactosamine.

As an alternative to expression in COS cells, recombinant α1,3GT may be expressed in bacteria using commercially available vectors.

To effect addition of α-galactosyl epitopes to virions, virus purified to the extent necessary is incubated in the presence or absence of neuraminidase (depending upon the type of virus being used), and in the presence of α1,3GT and UDP-Gal (0.1 to 20 mM). Virus is then isolated by centrifugation and suspended in a pharmaceutically acceptable vaccination carrier. To determine the efficiency of the reaction for each type of virus, radioactive UDP-Gal can be used as a tracer. Virions so treated are next assessed for their ability to bind anti-Gal and their rate of phagocytosis is then determined in the assays described above.

The following studies illustrate the enzymatic synthesis of α-galactosyl epitopes on viruses and human cells.

Expression of recombinant α1,3GT in bacteria.

The XPRESS SYSTEM™ of Invitrogen Corporation (San Diego, Calif.) was used according to the manufacturer's instructions to express recombinant (rec) α1,3GT in bacteria. The luminal portion of marmoset α1,3GT cDNA, cloned from a cDNA library (Henion et al., 1994, Glycobiology 4:193), was amplified by PCR (amino-acid 61–376 and the stop codon) and inserted into the pRSET vector (Invitrogen). This vector contains, upstream of the insert, a series of six histidine residues $(His)_6$, that enable the isolation of the fusion protein produced on a nickel column (Probond resin, Invitrogen). Bacteria (*E. coli* JM109) were transformed with the pRSET vector containing the α1,3GT insert, and colonies containing the insert were cloned based on growth in amphiciline and demonstration of the insert within the cloned plasmid. The bacteria were grown in 0.5 liter volumes and subjected to IPTG and M13/T7 phage infection for induction of α1,3GT synthesis, collected as pellets by centrifugation, lysed with lysozyme in 100 ml volume of PBS pH 6.3, sonicated and the supernatant passed through a nickel column (0.5 ml resin) according to XPRESS SYSTEM™ manuals of Invitrogen version 2.0 (Protein expression) and 1.9 (Protein purification). The enzyme was eluted from the column with 3 ml of 0.3M imidazole in saline and subjected to catalytic activity assay as described herein in the section entitled "Cloning and Characterization of marmoset 1,3GT". Ten μl rec. α1,3GT were brought to a final volume of 50 μin 0.1M MES buffer containing 25 mM $MnCl_2$, 10 μg N-acetyllactosamine and 0.2 μCi UDP-[$^3$H]Gal ($2\times10^5$cpm). The enzyme catalyses the reaction:

Galβ-4GlcNAc + UDP-[$^3$H]Gal —α1,3GT→
N-acetyllactosamine, Uridine diphosphate-galactose

[$^3$H]Galα1-3Galβ1+4GlcNAc + UDP
free α-galactosyl epitope, Uridine diphosphate The enzyme reaction was loaded on a DOWEX column which binds UDP-Gal but not the free α-galactosyl epitope. After passing 2 ml of water through the column, the radioactivity in the effluent was measured. In the absence of enzyme, only 300 cpm passed through the column, whereas in presence of the enzyme, 79,000 cpm were measured in the effluent. Based on a specific activity of 0.05 mCi/μmol of [3H] Gal, this radioactivity represents 0.03 nmol of the synthesized free α-galactosyl epitope.

Synthesis of aL-galactosyl epitopes on influenza virus.

The following demonstrates the de novo synthesis of α-galactosyl epitopes on viruses, using influenza virus as a model. Influenza virus has 5 to 7N-acetyllactosamine residues per hemagglutinin molecule (HA) (Kiel et al., 1985, Embo J. 4:2711; Deom et al., 1985, J. Biol. Chem. 260:14771). The influenza virus strain A/PR8/34 was grown in embryonated eggs, isolated from allantoic fluid and brought to a concentration of 1 mg/ml. By performing an enzyme assay with 10 μg of virus in 50 μl volumes of enzyme reaction, as described above, it is possible to measure the transfer of [$^3$H]Gal from UDP-[$^3$H]Gal to N-acetyllactosamine on the virions for the formation of α-galactosyl epitopes. After 2 hours incubation at 37° C., the virus was precipitated with cold 5% trichloroacetic acid, harvested on filters and monitored for radioactivity in a scintillation counter. The results are shown in FIG. 15. Based on the specific activity of [$^3$H]Gal and the amount of $10^9$ virions in 10 μg virus, the obtained radioactivity of 68,000 cpm (FIG. 15) is equivalent to the de novo synthesis of 1100 α-galactosyl epitopes per virion. As shown in FIG. 15, control preparations containing no enzyme or no virus contained minimal background radiation.

In order to demonstrate the binding of the anti-Gal to these de novo synthesized α-galactosyl epitopes, 100 μg of the influenza virus were subjected to α1,3GT activity in a total volume of 1 ml containing 100 μl of rec. α1,3GT and lmM of non-radiolabeled UDP-Gal. A similar enzyme reaction lacking UDP-Gal was used as control. Another control was the original virus not exposed to α1,3GT. After a 4 hour incubation at 37° C., the suspension containing the virus and α1,3GT were dialyzed overnight against 2 liters of saline in order to remove the nonutilized UDP-Gal and imidazole. Subsequently, the virus was dried in microtiter wells (1 μg virus per well), the wells blocked with 1% bovine serum albumin (BSA) in PBS for 2 hours at 37° C., and studied for anti-Gal binding according to the assay described above in the section-entitled "Demonstration of α-galactosylGalactosyl Epitopes on PR8 Virus". Biotinylated anti-Gal was administered at various concentrations into the wells and incubated for 2 hours at 24° C. Subsequently, the plates were washed with PBS—0.05% Tween and peroxidase-conjugated avidin was added to the wells. The plates were incubated for 1 hour at 24° C., washed, and color reaction developed with O-phenylenediamine. The peroxidase reaction was stopped after 30 minutes with 1M sulfuric acid and absorbance measured at 492 nm in an ELISA reader. Biotinylated anti-Gal was pretreated with neuraminidase to remove sialic acid from the antibody carbohydrate chains, in order to prevent nonspecific binding of the antibody to the hemagglutinin molecule on the virus via the terminal sialic acid on the carbohydrate chain.

As shown in FIG. 16A, anti-Gal readily bound to the virus subjected to α-galactosyl epitopes synthesis (—○—). However, only marginal nonspecific binding was observed with the virus from the enzyme reaction lacking the substrate UDP-Gal (—□—), and with the untreated virus (Δ). In parallel studies, the binding of the lectin *Bandeiraea simplicifolia* $IB_4$ (BS lectin) to the various virus preparations was studied. This lectin, like anti-Gal, interacts specifically with α-galactosyl epitopes (Wood et al, 1979, Arch. Biochem.

Biophys. 198:1). It was observed (FIG. 16B) that the biotinylated BS lectin readily bound to the virus with α-galactosyl epitopes (—○—) but not to the original virus (—Δ—) or to the control virus in the enzyme reaction which lacked UDP-Gal (—□—). These findings further support the observation of α-galactosyl epitope synthesis on influenza virus subjected to α1,3GT activity. Overall, these findings indicate that the rec α1,3GT produced in bacteria can synthesize as many as 1100 α-galactosyl epitopes per virion of influenza virus, and that these epitopes can readily interact with anti-Gal.

Synthesis of α-galactosyl epitopes on human red cells.

As a first step for the synthesis of α-galactosyl epitopes on human tumor cells by rec. α1,3GT, the synthesis of these epitopes was studied with human red cells of blood type O. Unlike influenza virus, where N-acetyllactosamine is the terminal structure on the carbohydrate chains of the envelope glycoproteins (i.e., Galβ1-4GlcNAc-R), in humans many of N-acetyllactosamine residues are capped, mostly by sialic acid (SA) in the form of SA-Galβ1-4GlcNAc-R. Thus, in order to expose the N-acetyllactosamine residues, the red cells (10% vol/vol) in saline with 1 mN CaCl$_2$) were first subjected to neuraminidase activity (Vibrio cholera neuraminidase [VCN], Sigma, final concentration 0.02 units/ml) for 1 hour at 37° C., so that the sialic acid was removed in the reaction:

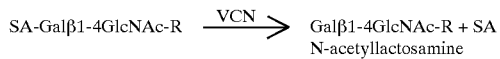

Subsequently, the intact red cells (10 μl/of 10% vol/vol) were subjected to the α1,3GT reaction in a 50 μl volume, containing 10l α1,3GT, VCN-treated red cells (10 μl) or untreated red cells (10 μl). As shown in FIG. 17, approximately 14,000 cpm of [$^3$H]Gal were linked by rec. α1,3GT to VCN-treated red cells (FIG. 17, "RED CELLS (VCN)", whereas only three fold less were linked to the nontreated red cells (FIG. 17, "RED CELLS"). This indicates that VCN indeed exposed many N-acetyllactosamine residues that are penultimate to the sialic acid, and that α1,3GT linked terminal α-galactosyl units to these residues. Based on the specific activity of [$^3$H]Gal and the number of red cells per reaction (10$^7$ cells) it is estimated that α1,3GT synthesizes approximately 2.5×10$^4$ α-galactosyl epitopes per red cell.

These de novo synthesized α-galactosyl epitopes on the red cells can readily interact with anti-Gal and with ES lectin. This was demonstrateded by the synthesis of α-galactosyl epitopes on the VCN-treated red cells in a 1 ml enzyme reaction containing 100 μl of rec. α1,3GT, 100 μVCN-treated red cells and 1 mM cold (i.e., nonradioactive) UDP-Gal. After 2 hours incubation at 37° C., the red cells were washed and studied for binding biotinylated anti-Gal (5 μg/ml) or biotinylated BS lectin (20 μg/ml), followed by $^{125}$I-avidin. As shown in FIG. 18, 1×10$^7$ VCN-treated red cells, subjected to α-galactosyl epitope synthesis, readily bound anti-Gal ("ANTI-GAL") and ES lectin ("BS LECTIN"), whereas the same red cells which lacked α-galactosyl epitopes, i.e., were not incubated with rec. α1,3GT, ("ANTI-GAL CONTROL"; "ES-LECTIN CONTROL") displayed only marginal binding of the antibody or the lectin.

For further demonstration of anti-Gal binding to α-galactosyl epitopes synthesized on the VCN-treated red cells, the red cells were lysed and their membranes dried in microtiter wells (approximately 3×10$^5$ red cells per well), then fixed to the plates with 0.2% glutaraldehyde. The plates were then blocked with 0.1M glycine followed by 1% BSA in PBS and subjected to an ELISA assay with biotinylated anti-Gal and BS lectin followed by avidin-peroxidase. As shown in FIG. 19A, anti-Gal readily bound to the VCN-treated red cells which had de novo synthesized α-galactosyl epitopes (—○—), whereas only background binding was observed in the control VCN- treated red cells (—□—). Similar differential binding was observed with BS lectin (FIG. 19B), which bound to the red cells with α-galactosyl epitopes (—○—), but not to the control red cells (—□—)

These data indicate that subsequent to the removal of sialic acid from red cells by neuraminidate, rec. α1,3GT can synthesize α-galactosyl epitopes on the exposed N-acetyllactosamine residues. Since similar carbohydrate chains are present on human tumor cells, the same procedure (i.e., VCN followed by α1,3GT) may be applied to freshly isolated tumor cells or tumor cell membrane, to synthesize α-galactosyl epitopes. Upon immunization, these epitopes will bind anti-Gal and thus become opsonized for effective uptake, processing, and presentation of the tumor associated antigens by antigen presenting cells.

Because of the unique reciprocal distribution of anti-Gal in animals, the augmenting effect of α-galactosyl epitopes on tumor immunogenicity cannot be examined in the usual experimental animal models since non-primate mammals produce autologous α-galactosyl epitopes and thus lack anti-Gal antibodies. Old World monkeys are also unsuitable for such immunization studies because of the need to test syngeneic tumors. Thus, the only potential experimental animal model is mice in which the gene for α1,3 galactosyltransferase can be inactivated (Galili, 1992, Immunol. Today 14:480). However, it is not yet clear whether mice lacking α-galactosyl epitopes are viable. It should be stressed that the proposed immunization studies involve irradiated autologous cells, killed viral vaccines, and other non-replicating antigens. Since it is known that humans are routinely exposed to GSL molecules through nutrition there are no apparent risks in vaccination of patients with either their own autologous irradiated malignant cells or with viruses pretreated to express α-galactosyl epitopes.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A method of opsonizing a tumor cell in an anti-Gal-synthesizing animal having a tumor comprising
   obtaining said cell from said animal;
   incubating said cell in the presence of a preparation of α-galactosyl epitope containing glycosphingolipids to effect insertion of said α-galactosyl epitopes into the membrane of said cell;
   irradiating said α-galactosyl epitope containing cell; and,
   administering said α-galactosyl epitope containing cell to said animal.

2. A method of opsonizing a tumor associated antigen in an anti-Gal-synthesizing animal having a tumor comprising
   obtaining a tumor associated antigen containing cell from said animal;
   extracting the cell membrane of said cell;
   incubating said cell membrane in the presence of α-galactosyl epitope containing glycosphingolipids to effect insertion of said α-galactosyl epitopes into said membrane;
   administering said α-galactosyl epitope containing membrane to said animal.

3. A method of opsonizing a tumor associated antigen in an anti-Gal synthesizing animal having a tumor comprising
   obtaining a tumor associated antigen containing cell from said animal;
   incubating said cell in the presence of neuramini- dase;
   further incubating said cell in the presence of α1,3 galactosyltransferase and UDP-galactose to effect addition of α-galactosyl epitopes to said tumor associated antigens;
   irradiating said cell so incubated; and
   administering said α-galactosyl epitope containing cell to said animal.

4. A method of opsonizing a tumor associated antigen an anti-Gal synthesizing animal having a tumor comprising
   obtaining a tumor associated antigen containing cell from said animal;
   extracting the cell membrane of said cell;
   incubating said cell membrane in the presence of neuraminidase;
   further incubating said cell membrane in the presence of α1,3 galactosyltransferase and UDP-galactose to effect addition of α-galactosyl epitopes to said tumor associated antigen;
   administering said cell membrane so incubated to said animal.

5. The method of claim 1, 2, 3, or 4, wherein said animal is selected from the group consisting of birds, Old World monkeys and humans.

6. The method of claim 5, wherein said animal is a human.

7. The method of claim 1, 2, 3, or 4, wherein said tumor is selected from the group consisting of leukemia, lymphoma, myeloma, melanoma, ovarian carcino- ma, lung carcinoma, mammary carcinoma, thyroid carcino- ma, colon carcinoma and sarcoma.

8. The method of claim 7, wherein said tumor is leukemia.

9. The method of claim 1 or 2, wherein said animal is treated with an adjuvant prior to administration of said α-galactosyl epitope containing cell.

10. The method of claim 3, wherein said animal is treated with an adjuvant prior to administration of said α-galactosyl epitope containing epitope.

11. The method of claim 4, wherein said animal is treated with an adjuvant prior to administration of said cell membrane.

12. A preparation comprising tumor cells or tumor cell membranes of an anti-Gal synthesizing animal having a tumor, wherein said tumor cells or tumor cell membranes comprise α-galactosyl epitopes.

13. The preparation of claim 12, wherein said animal is selected from the group consisting of birds, Old World monkeys and humans.

14. The preparation of claim 12, wherein said animal is a human.

15. The preparation of claim 12, wherein said tumor is selected from the group consisting of leukemia, lymphoma, myeloma, melanoma, ovarian carcinoma, lung carcinoma, mammary carcinoma, thyroid carcinoma, colon carcinoma and sarcoma.

16. The preparation of claim 12, wherein said tumor is leukemia.

17. A method of opsonizing a tumor associated antigen in an anti-Gal synthesizing animal comprising
   providing a complex comprising an α-galactosyl epitope, said tumor associated antigen and a lipid bilayer, and
   administering an immunizing effective amount of said complex to said animal.

18. The method of claim 17, wherein said tumor associated antigen is juxtaposed to said lipid bilayer in said complex.

19. The method of claim 18, wherein said α-galactosyl epitope is inserted in said lipid bilayer.

20. The method of claim 18, wherein said α-galactosyl epitope is encapsulated in said lipid bilayer.

21. A method of opsonizing a tumor associated antigen in an anti-Gal synthesizing animal comprising
   encapsulating said tumor associated antigen in a lipid bilayer to form a complex;
   incubating said complex in the presence of α-galactosyl epitope containing glycosphingolipids to effect insertion of said α-galactosyl epitopes into said lipid bilayer;
   administering said complex so incubated to said animal.

22. The method of claim 17 or 21, wherein said animal is treated with an adjuvant prior to administration of said complex.

23. The method of claim 17 or 21, wherein said animal is selected from the group consisting of birds, Old World monkeys and humans.

24. The method of claim 23, wherein said animal is a human.

25. A method according to claim 21 wherein said complex is contained in a cell or cell membrane fragment.

* * * * *

UNITED STATES PATENT AND TRADEMARK OFFICE
CERTIFICATE OF CORRECTION

PATENT NO. : 5,879,675

DATED : March 9, 1999

INVENTOR(S) : Uri Galili

It is certified that error appears in the above-identified patent and that said Letters Patent is hereby corrected as shown below:

ON THE TITLE PAGE
Item [75] Inventors should read --Uri Galili, Wayne PA

Signed and Sealed this

Eighth Day of June, 1999

Attest:

Q. TODD DICKINSON

*Attesting Officer*    Acting Commissioner of Patents and Trademarks

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1140 base pairs
        ( B ) TYPE: nucleic acid
        ( C ) STRANDEDNESS: double
        ( D ) TOPOLOGY: linear (  i  i  ) MOLECULE TYPE: cDNA (  i  x  ) FEATURE:
    (  A  ) NAME/KEY: CDS
    (  B  ) LOCATION: 10..1140

(  x  i  ) SEQUENCE DESCRIPTION: SEQ ID NO:1:

```
GAGAAAATA ATG AAT GTC AAA GGA AAA GTA ATT CTG TCG ATG CTG GTT          48
          Met Asn Val Lys Gly Lys Val Ile Leu Ser Met Leu Val
            1               5                  10

GTC TCA ACT GTG ATT GTT GTG TTT TGG GAA TAT ATC AAC AGC CCA GAA         96
Val Ser Thr Val Ile Val Val Phe Trp Glu Tyr Ile Asn Ser Pro Glu
     15              20                  25

GGC TCT TTC TTG TGG ATA TAT CAC TCA AAG AAC CCA GAA GTT GAT GAC        144
Gly Ser Phe Leu Trp Ile Tyr His Ser Lys Asn Pro Glu Val Asp Asp
 30              35                  40                   45

AGC AGT GCT CAG AAG GAC TGG TGG TTT CCT GGC TGG TTT AAC AAT GGG        192
Ser Ser Ala Gln Lys Asp Trp Trp Phe Pro Gly Trp Phe Asn Asn Gly
             50                   55                   60

ATC CAC AAT TAT CAA CAA GAG GAA GAA GAC ACA GAC AAA GAA AAA GGA        240
Ile His Asn Tyr Gln Gln Glu Glu Glu Asp Thr Asp Lys Glu Lys Gly
                 65                   70                  75

AGA GAG GAG GAA CAA AAA AAG GAA GAT GAC ACA ACA GAG CTT CGG CTA        288
Arg Glu Glu Glu Gln Lys Lys Glu Asp Asp Thr Thr Glu Leu Arg Leu
             80                   85                   90

TGG GAC TGG TTT AAT CCA AAG AAA CGC CCA GAG GTT ATG ACA GTG ACC        336
Trp Asp Trp Phe Asn Pro Lys Lys Arg Pro Glu Val Met Thr Val Thr
         95                  100                 105

CAA TGG AAG GCG CCG GTT GTG TGG GAA GGC ACT TAC AAC AAA GCC ATC        384
Gln Trp Lys Ala Pro Val Val Trp Glu Gly Thr Tyr Asn Lys Ala Ile
110              115                 120                 125

CTA GAA AAT TAT TAT GCC AAA CAG AAA ATT ACC GTG GGG TTG ACG GTT        432
Leu Glu Asn Tyr Tyr Ala Lys Gln Lys Ile Thr Val Gly Leu Thr Val
                 130                 135                 140

TTT GCT ATT GGA AGA TAT ATT GAG CAT TAC TTG GAG GAG TTC GTA ACA        480
Phe Ala Ile Gly Arg Tyr Ile Glu His Tyr Leu Glu Glu Phe Val Thr
             145                 150                 155

TCT GCT AAT AGG TAC TTC ATG GTC GGC CAC AAA GTC ATA TTT TAT GTC        528
Ser Ala Asn Arg Tyr Phe Met Val Gly His Lys Val Ile Phe Tyr Val
         160                 165                 170

ATG GTG GAT GAT GTC TCC AAG GCG CCG TTT ATA GAG CTG GGT CCT CTG        576
Met Val Asp Asp Val Ser Lys Ala Pro Phe Ile Glu Leu Gly Pro Leu
175              180                 185

CGT TCC TTC AAA GTG TTT GAG GTC AAG CCA GAG AAG AGG TGG CAA GAC        624
Arg Ser Phe Lys Val Phe Glu Val Lys Pro Glu Lys Arg Trp Gln Asp
190              195                 200                 205

ATC AGC ATG ATG CGT ATG AAG ACC ATC GGG GAG CAC ATC TTG GCC CAC        672
Ile Ser Met Met Arg Met Lys Thr Ile Gly Glu His Ile Leu Ala His
                 210                 215                 220

ATC CAA CAC GAG GTT GAC TTC CTC TTC TGC ATG GAT GTG GAC CAG GTC        720
Ile Gln His Glu Val Asp Phe Leu Phe Cys Met Asp Val Asp Gln Val
             225                 230                 235

TTC CAA GAC CAT TTT GGG GTA GAG ACC CTG GGC CAG TCG GTG GCT CAG        768
Phe Gln Asp His Phe Gly Val Glu Thr Leu Gly Gln Ser Val Ala Gln
         240                 245                 250

CTA CAG GCC TGG TGG TAC AAG GCA GAT CCT GAT GAC TTT ACC TAT GAG        816
Leu Gln Ala Trp Trp Tyr Lys Ala Asp Pro Asp Asp Phe Thr Tyr Glu
255                  260                 265

AGG CGG AAA GAG TCG GCA GCA TAT ATT CCA TTT GGC CAG GGG GAT TTT        864
Arg Arg Lys Glu Ser Ala Ala Tyr Ile Pro Phe Gly Gln Gly Asp Phe
270                  275                 280                 285
```

| | | | | | | | | | | | | | | | | |
|---|---|---|---|---|---|---|---|---|---|---|---|---|---|---|---|---|
| TAT | TAC | CAT | GCA | GCC | ATT | TTT | GGA | GGA | ACA | CCG | ATT | CAG | GTT | CTC | AAC | 912 |
| Tyr | Tyr | His | Ala | Ala | Ile | Phe | Gly | Gly | Thr | Pro | Ile | Gln | Val | Leu | Asn | |
| | | | 290 | | | | | 295 | | | | | 300 | | | |
| ATC | ACC | CAG | GAG | TGC | TTT | AAG | GGA | ATC | CTC | CTG | GAC | AAG | AAA | AAT | GAC | 960 |
| Ile | Thr | Gln | Glu | Cys | Phe | Lys | Gly | Ile | Leu | Leu | Asp | Lys | Lys | Asn | Asp | |
| | | | 305 | | | | | 310 | | | | | 315 | | | |
| ATA | GAA | GCC | GAG | TGG | CAT | GAT | GAA | AGC | CAC | CTA | AAC | AAG | TAT | TTC | CTT | 1008 |
| Ile | Glu | Ala | Glu | Trp | His | Asp | Glu | Ser | His | Leu | Asn | Lys | Tyr | Phe | Leu | |
| | | | 320 | | | | | 325 | | | | | 330 | | | |
| CTC | AAC | AAA | CCC | TCT | AAA | ATC | TTA | TCT | CCA | GAA | TAC | TGC | TGG | GAT | TAT | 1056 |
| Leu | Asn | Lys | Pro | Ser | Lys | Ile | Leu | Ser | Pro | Glu | Tyr | Cys | Trp | Asp | Tyr | |
| | | 335 | | | | | 340 | | | | | 345 | | | | |
| CAT | ATA | GGC | CTG | CCT | TCA | GAT | ATT | AAA | ACT | GTC | AAG | CTA | TCA | TGG | CAA | 1104 |
| His | Ile | Gly | Leu | Pro | Ser | Asp | Ile | Lys | Thr | Val | Lys | Leu | Ser | Trp | Gln | |
| 350 | | | | | 355 | | | | | 360 | | | | | 365 | |
| ACA | AAA | GAG | TAT | AAT | TTG | GTT | AGA | AAG | AAT | GTC | TGA | | | | | 1140 |
| Thr | Lys | Glu | Tyr | Asn | Leu | Val | Arg | Lys | Asn | Val | * | | | | | |
| | | | | 370 | | | | | 375 | | | | | | | |

(2) INFORMATION FOR SEQ ID NO:2:

(i) SEQUENCE CHARACTERISTICS:
        (A) LENGTH: 376 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asn Val Lys Gly Lys Val Ile Leu Ser Met Leu Val Val Ser Thr
 1               5                  10                  15

Val Ile Val Val Phe Trp Glu Tyr Ile Asn Ser Pro Glu Gly Ser Phe
                20                  25                  30

Leu Trp Ile Tyr His Ser Lys Asn Pro Glu Val Asp Asp Ser Ser Ala
            35                  40                  45

Gln Lys Asp Trp Trp Phe Pro Gly Trp Phe Asn Asn Gly Ile His Asn
        50                  55                  60

Tyr Gln Gln Glu Glu Glu Asp Thr Asp Lys Glu Lys Gly Arg Glu Glu
65                  70                  75                  80

Glu Gln Lys Lys Glu Asp Asp Thr Thr Glu Leu Arg Leu Trp Asp Trp
                85                  90                  95

Phe Asn Pro Lys Lys Arg Pro Glu Val Met Thr Val Thr Gln Trp Lys
                100                 105                 110

Ala Pro Val Val Trp Glu Gly Thr Tyr Asn Lys Ala Ile Leu Glu Asn
            115                 120                 125

Tyr Tyr Ala Lys Gln Lys Ile Thr Val Gly Leu Thr Val Phe Ala Ile
        130                 135                 140

Gly Arg Tyr Ile Glu His Tyr Leu Glu Glu Phe Val Thr Ser Ala Asn
145                 150                 155                 160

Arg Tyr Phe Met Val Gly His Lys Val Ile Phe Tyr Val Met Val Asp
                165                 170                 175

Asp Val Ser Lys Ala Pro Phe Ile Glu Leu Gly Pro Leu Arg Ser Phe
            180                 185                 190

Lys Val Phe Glu Val Lys Pro Glu Lys Arg Trp Gln Asp Ile Ser Met
        195                 200                 205

Met Arg Met Lys Thr Ile Gly Glu His Ile Leu Ala His Ile Gln His
        210                 215                 220

Glu Val Asp Phe Leu Phe Cys Met Asp Val Asp Gln Val Phe Gln Asp
225                 230                 235                 240
```

| | | | | | | | | | | | | | | |
|---|---|---|---|---|---|---|---|---|---|---|---|---|---|---|
| His | Phe | Gly | Val | Glu<br>245 | Thr | Leu | Gly | Gln | Ser<br>250 | Val | Ala | Gln | Leu<br>255 | Gln Ala |
| Trp | Trp | Tyr | Lys<br>260 | Ala | Asp | Pro | Asp<br>265 | Phe | Thr | Tyr | Glu | Arg<br>270 | Arg | Lys |
| Glu | Ser | Ala<br>275 | Ala | Tyr | Ile | Pro<br>280 | Phe | Gly | Gln | Gly | Asp<br>285 | Phe | Tyr | Tyr His |
| Ala | Ala<br>290 | Ile | Phe | Gly | Gly | Thr<br>295 | Pro | Ile | Gln | Val | Leu<br>300 | Asn | Ile | Thr Gln |
| Glu<br>305 | Cys | Phe | Lys | Gly | Ile<br>310 | Leu | Leu | Asp | Lys | Lys<br>315 | Asn | Asp | Ile | Glu Ala<br>320 |
| Glu | Trp | His | Asp | Glu<br>325 | Ser | His | Leu | Asn | Lys<br>330 | Tyr | Phe | Leu | Leu | Asn Lys<br>335 |
| Pro | Ser | Lys | Ile<br>340 | Leu | Ser | Pro | Glu | Tyr<br>345 | Cys | Trp | Asp | Tyr | His<br>350 | Ile Gly |
| Leu | Pro | Ser<br>355 | Asp | Ile | Lys | Thr | Val<br>360 | Lys | Leu | Ser | Trp | Gln<br>365 | Thr | Lys Glu |
| Tyr | Asn<br>370 | Leu | Val | Arg | Lys | Asn<br>375 | Val | | | | | | | |

( 2 ) INFORMATION FOR SEQ ID NO:3:

( i ) SEQUENCE CHARACTERISTICS:
        ( A ) LENGTH: 1131 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

```
ATGAATGTCA AGGGAAAAGT GATCCTGTTG ATGCTGATTG TCTCAACCGT GGTTGTCGTG      60
TTTTGGGAAT ATGTCAACAG CCCAGACGGC TCTTTCTTGT GGATATATCA CACAAAAATT     120
CCAGAGGTTG GTGAGAACAG ATGGCAGAAG GACTGGTGGT TCCCAAGCTG GTTTAAAAAT     180
GGGACCCACA GTTATCAAGA AGACAACGTA GAAGGACGGA GAGAAAGGG TAGAAATGGA      240
GATCGCATTG AGGAAGATGA CACAACAGAG CCTCAGCTAT GGGACTGGTT CAATCCAAAG     300
AACCGCCCGG ATGTTTTGAC AGTGACCCCG TGGAAGGCGC CGATTGTGTG GAAGGCACT      360
TATGACACAG CTCTGCTGGA AAAGTACTAC GCCACACAGA AACTCACTGT GGGGCTGACA     420
GTGTTTGCTG TGGGAAAGTA CATTGAGCAT TACTTAGAAG ACTTTCTGGA GTCTGCTGAC     480
ATGTACTTCA TGGTTGGCCA TCGGGTCATA TTTTACGTCA TGATAGACGA CACCTCCCGG     540
ATGCCTGTCG TGCACCTGAA CCCTCTACAT TCCTTACAAG TCTTTGAGAT CAGGTCTGAG     600
AAGAGGTGGC AGGATATCAG CATGATGCGC ATGAAGACCA TTGGGGAGCA CATCCTGGCC     660
CACATCCAGC ACGAGGTCGA CTTCCTCTTC TGCATGGACG TGGATCAAGT CTTTCAAGAC     720
AACTTCGGGG TGGAAACTCT GGGCCAGCTG GTAGCACAGC TCCAGGCCTG GTGGTACAAG     780
GCCAGTCCCG AGAACTTCAC CTATGAGAGG CGGGAACTGT CGGCCGCGTA CATTCCATTC     840
GGAGAGGGGG ATTTTTACTA CCACGCGGCC ATTTTTGGAG GAACGCCTAC TCACATTCTC     900
AACCTCACCA GGGAGTGCTT TAAGGGGATC CTCCAGGACA AGAAACATGA CATAGAAGCC     960
CAGTGGCATG ATGAGAGCCA CCTCAACAAA TACTTCCTTT TCAACAAACC CACTAAAATC    1020
CTATCTCCAG AGTATTGCTG GGACTATCAG ATAGGCCTGC CTTCAGATAT TAAAAGTGTC    1080
AAGGTAGCTT GGCAGACAAA AGAGTATAAT TTGGTTAGAA ATAATGTCTG A            1131
```